United States Patent [19]

Schreiber et al.

[11] 4,107,208
[45] Aug. 15, 1978

[54] TETRAMETHYL-HEXAHYDROACETONAPHTHONES

[75] Inventors: William L. Schreiber, Jackson; James N. Siano, Keyport, both of N.J.; Edward J. Shuster, Brooklyn, N.Y.

[73] Assignee: International Flavors & Fragrances Inc., Union Beach, N.J.

[21] Appl. No.: 834,500

[22] Filed: Sep. 19, 1977

Related U.S. Application Data

[63] Continuation-in-part of Ser. No. 740,890, Nov. 11, 1976, Pat. No. 4,076,749.

[51] Int. Cl.$^2$ .............................................. C07C 49/61
[52] U.S. Cl. ............................ 260/586 F; 260/586 C
[58] Field of Search ........................ 260/586 C, 586 F

[56] References Cited

U.S. PATENT DOCUMENTS 3,911,018  10/1975  Hall et al. ...................... 260/586 F
3,965,186  6/1976   Hall ................................ 260/586 F

FOREIGN PATENT DOCUMENTS 896,039  5/1962  United Kingdom ................ 260/586 F

OTHER PUBLICATIONS

Kagi et al, "J. Soc. Cos. Chem.", 1973, 1-14.

*Primary Examiner*—Norman Morgenstern
*Attorney, Agent, or Firm*—Arthur L. Liberman; Harold Haidt; Franklin D. Wolffe

[57] ABSTRACT

Described are hexahydrotetramethyl acetonaphthones and mixtures of such substituted acetonaphthones having the generic formula:

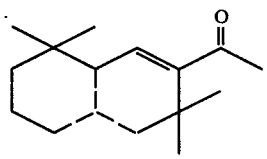

wherein one of the dashed lines is a carbon-carbon double bond and each of the other of the dashed lines is a carbon-carbon single bond.

The products produced are useful as vetiver ingredients in perfumes and perfumed articles.

2 Claims, 13 Drawing Figures

NMR SPECTRUM FOR EXAMPLE II (B)
SOLVENT: CDCL3
SWEEP WIDTH: 1000 cps.

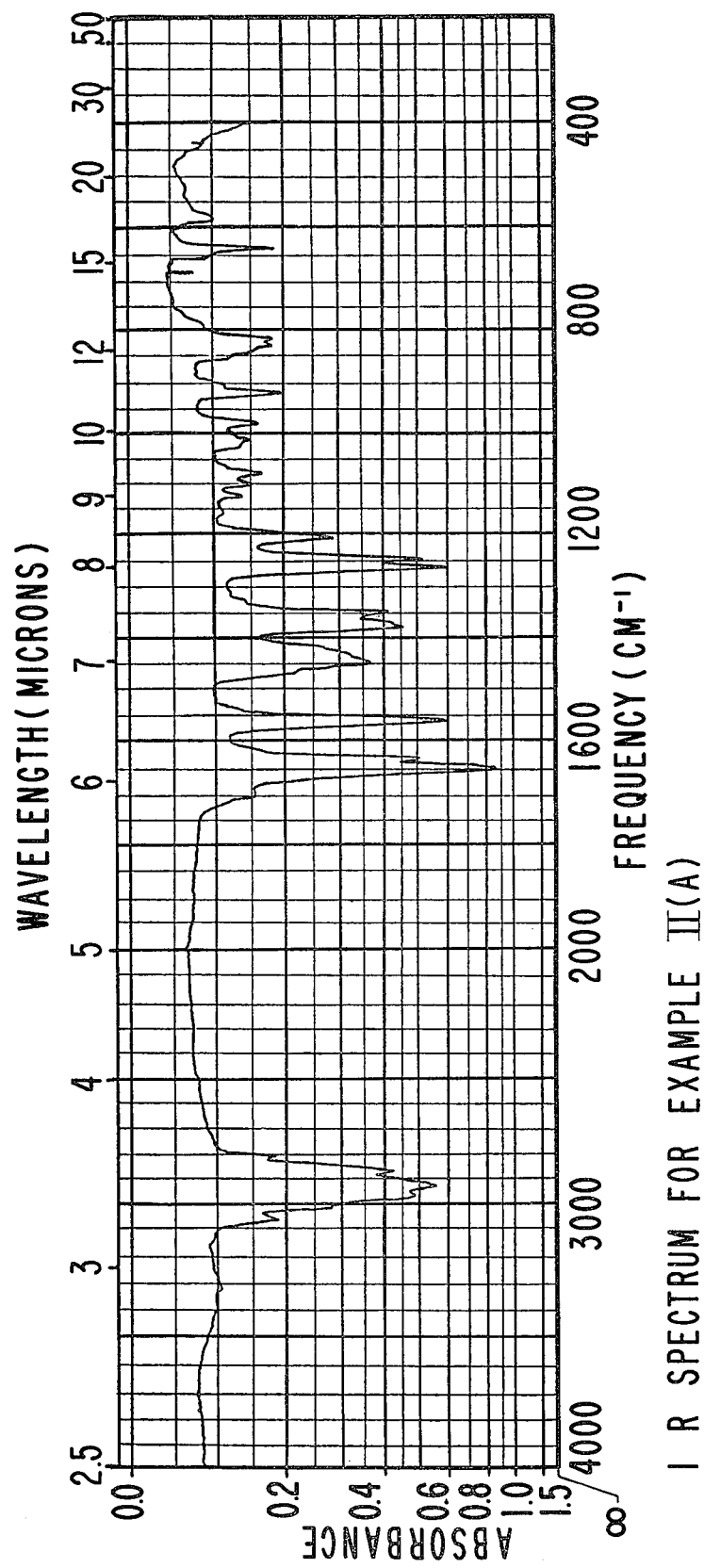

GC PROFILE FOR EXAMPLE II(c)

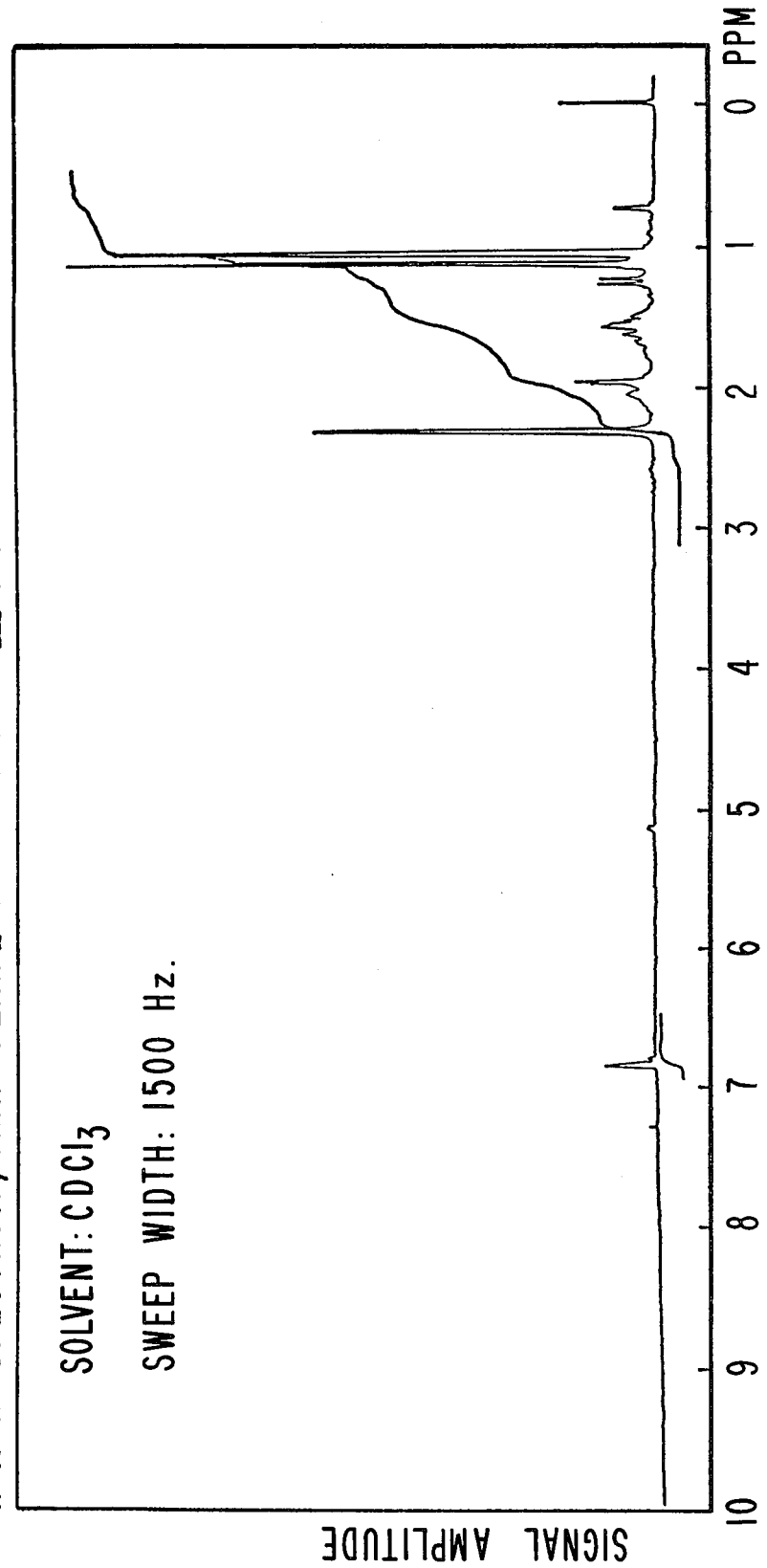
FIG.5 NMR SPECTRUM, TRAP-PEAK I FOR EXAMPLE II(C) FRACTION 4.
SOLVENT: CDCl₃
SWEEP WIDTH: 1500 Hz.

IR SPECTRUM FOR TRAP PEAK I EXAMPLE II(C), FRACTION 4

FIG. 8  I R SPECTRUM TRAP PEAK II FOR EXAMPLE II(C), FRACTION 4.

IR SPECTRUM TRAP PEAK I FOR EXAMPLE III (A)

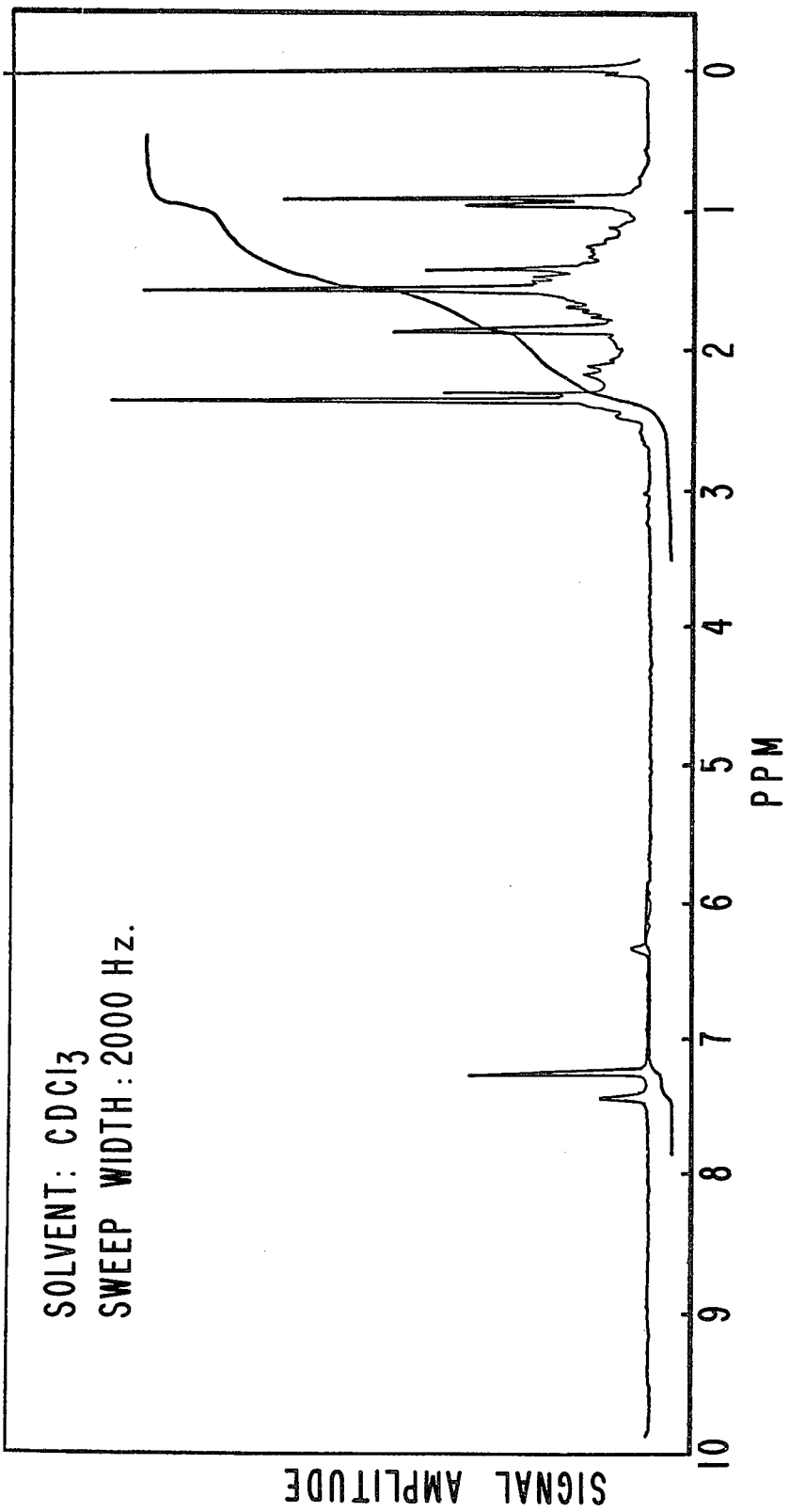

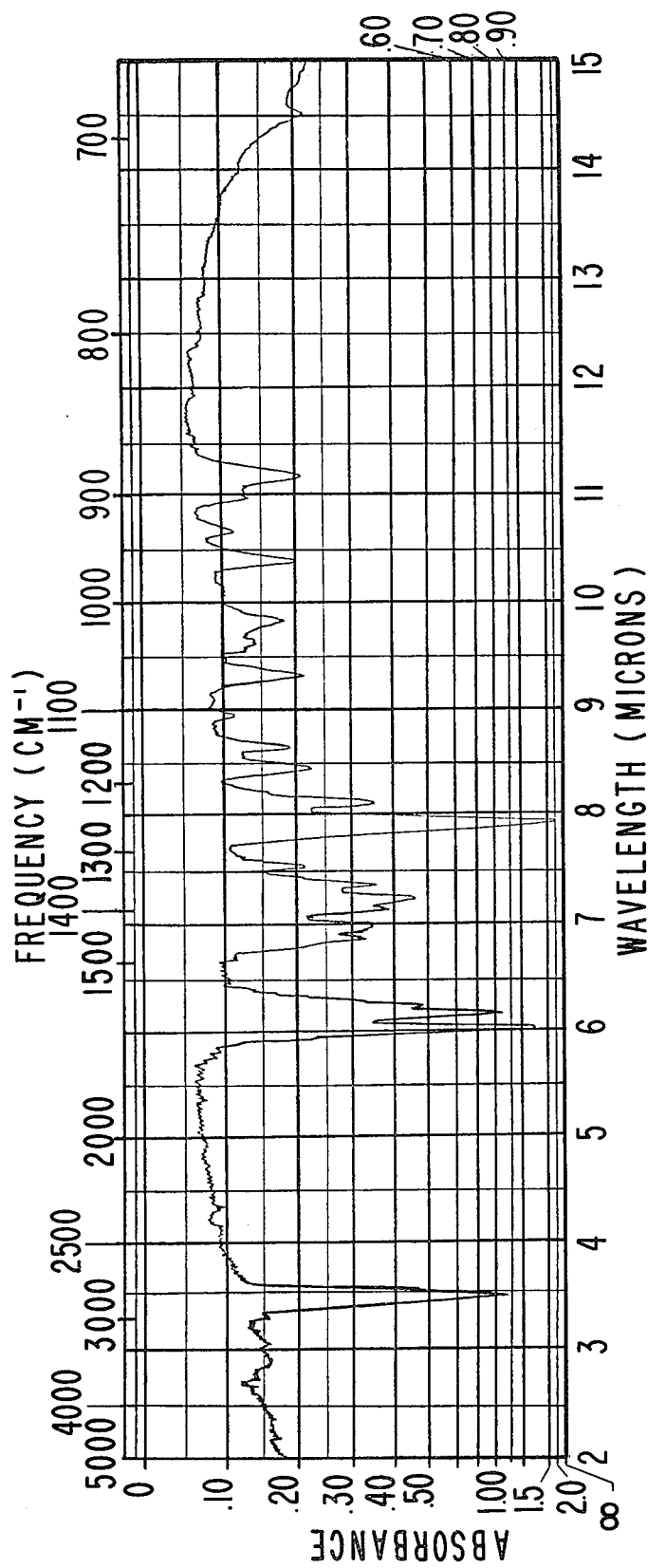

TETRAMETHYL-HEXAHYDROACETONAPHTHONES

This appication is a continuation-in-part of Application for U.S. Ser. No. 740,890 filed on Nov. 11, 1976 now U.S. Pat. No. 4,076,749.

BACKGROUND OF THE INVENTION

Materials which can provide aromas with sweet woody, citrusy, vetiver, musky, woody/peppery, woody/leathery, hay and green nuances and/or woody fragrance notes are known in the art of perfumery. Natural materials which provide such fragrances and contribute desired nuances to perfumery compositions, such as natural vetiver oil, are frequently difficult to obtain and/or are high in cost or vary in quality from one batch to another and/or are generally subject to the usual variations of natural products.

There is accordingly a continuing effort to find synthetic materials which will replace the essential fragrance notes provided by natural essential oils or compositions thereof having a vetiver aroma. Unfortunately, many of these synthetic materials either have the desired nuances only to a relatively small degree or else contribute undesirable or unwanted odor to the composition. The search for materials which can provide a more refined vetiver fragrance has been difficult and relatively costly in the areas of both natural products and synthetic products.

Acetonaphthones, particularly octahydro acetonaphthone, are known in perfumery particularly for providing amber or fruity amber fragrance notes which do not discolor with age. Thus, U.S. Pat. No. 3,911,018, issued on Oct. 7, 1975, covers an isomer of octahydrotetramethyl acetonaphthone having the structure:

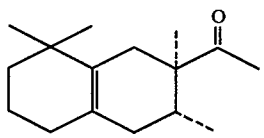

wherein the dashed lines represent methyl groups "cis" to one another.

U.S. Pat. No. 3,911,018 also covers processes for producing isomer mixtures of octahydro-2', 3', 8', 8'-tetramethyl-(2' or 3')-acetonaphthone having the generic formula:

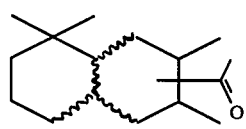

wherein one of the wavy lines is a carbon-carbon double bond and the other of the wavy lines represent carbon-carbon single bonds. The mixtures produced by the processes of U.S. Pat. No. 3,911,018 contain from 70 mole percent up to 99 mole percent of compounds having the generic structure:

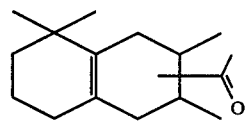

Such a generic structure includes individual compounds having an acetyl group at the 2' position, compounds having an acetyl group at the 3' position and mixtures of such compounds. The generic structures set forth above also include geometric isomers wherein the acetyl group is cis to the methyl group on the carbon atom adjacent to that bonded to the acetyl moiety and where the acetyl group is "trans" to the methyl group on the carbon atom adjacent to that bonded to the acetyl moiety. Furthermore, the products of U.S. Pat. No. 3,911,018 are indicated to be produced by means of a two-step reaction:

1. Reacting myrcene with 3-methyl-3-penten-2-one either:
   a. in the presence of a Lewis acid at temperatures in the range of from 0° up to 50° C thereby producing a mixture of geometric isomers which are Diels-Alder adducts which are alkenyl acetyl dimethyl substituted cyclohexenes represented by the structure:

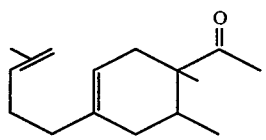

or:
   b. reacting myrcene with 3-methyl-3-penten-2-one without using a catalyst at temperatures in the range of 120° C up to 180° C forming a mixture of isomers (including geometric isomers) of alkenyl acetyl dimethyl substituted cyclohexenes having the generic structure:

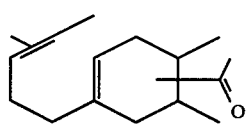

2. Cyclizing the resulting substituted cyclohexenes (Diels-Alder adducts) by means of heating same in the presence of phosphoric acid or dilute sulfuric acid (50-80%) or boron trifluoride or complexes thereof, e.g., boron trifluoride etherate.

Kagi, et al, Journal of the Society of Cosmetic Chemists, (Great Britain), 1973, pages 1-14, "Catalyzed Diels-Alder Reactions in the Synthesis of Perfumery Materials", discloses a synthesis of one of the isomers capable of being produced by the processes of the invention, which isomer has the structure:

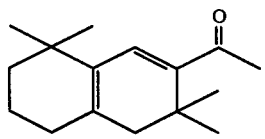

by means of reacting myrcene and 3-bromo-4-methyl-pent-3-ene-2-one to give the bromo adduct having the structure:

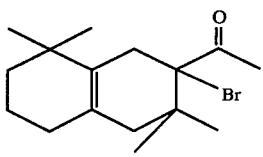

and then dehydrobrominating the said bromo adduct to give the dienone. Kagi, et al, reports that this particular isomer has "a very powerful, musk-ambergris odour" on page 10. The novel isomer as well as the mixture of isomers produced by the instant invention have properties which are advantageous and unexpected with respect to the particular isomer of Kagi, et al.

In addition, British Pat. No. 896,039 entitled "Method of Producing Derivatives of the 1,1-Dimethyl-octahydronaphthalene Series" discloses the generic process:

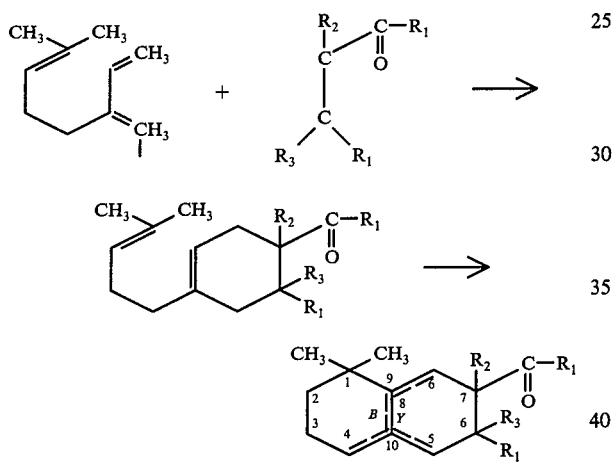

wherein $R_2$, $R_3$ and $R_4$ are disclosed to be the same or different and hydrogen or alkyl and $R_1$ is disclosed to be hydroxy, alkyl or alkoxy. The British patent discloses this process to be useful for producing products "resembling the well known class of violet perfumes". Indeed, Example 5 of the British patent alleges that the compound 1,1,6,6-Tetramethyl-7-ketomethyl-Octalin produced by (1) reacting myrcene and mesityl oxide thermally followed by (2) subsequent cyclization, has a pleasant "woody ambergris smell". However, a repetition of the teachings of this British patent gives rise to the following results:

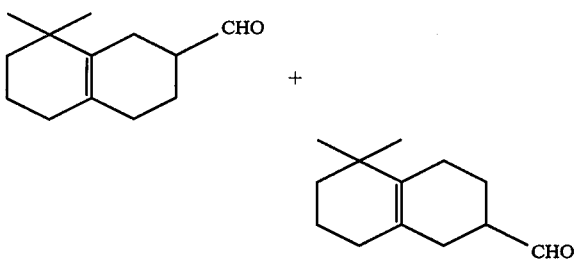

NAME

1',2',3',4',5',6',7',8'-octahydro-8',8' (and 5',5')dimethyl-2'-naphthaldehyde

PERFUME PROPERTIES

Green, fruity

STRUCTURE OF COMPOUND

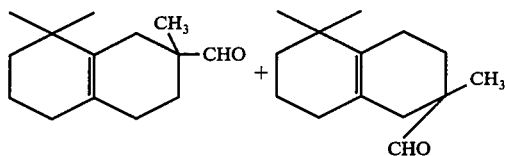

NAME 1',2',3',4',5',6',7',8'-octahydro-2',8',8'(and 2',5',5')-trimethyl-2', naphthaldehyde

PERFUME PROPERTIES

Green floral, fruity

STRUCTURE OF COMPOUND

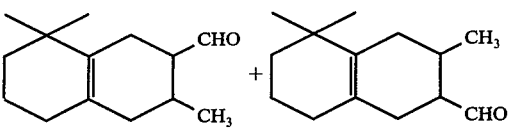

NAME

1',2',3',4',5',6',7',8'-octahydro-3',8',8'(and 3',5',5')-trimethyl-2'-naphthaldehyde

PERFUME PROPERTIES

Green, buttery, woody

STRUCTURE OF COMPOUND

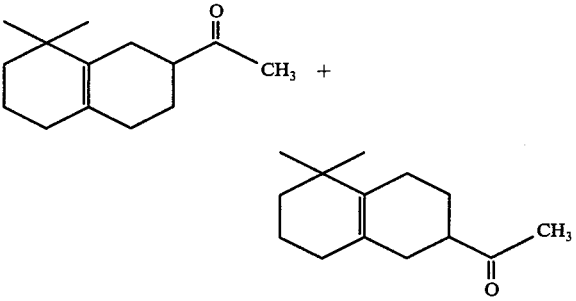

NAME

1',2',3',4',5',6',7',8'-octahydro-5',5'(and 8',8')-dimethyl-2'-acetonaphthone

PERFUME PROPERTIES

Ionone-like

STRUCTURE OF COMPOUND

-continued

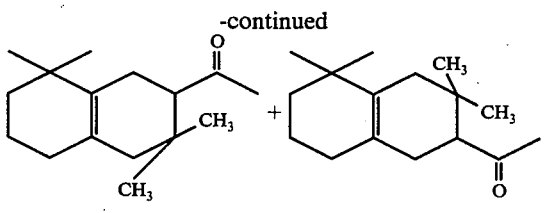

NAME

1',2',3',4',5',6',7',8'-octahydro-3',3',8',8'(and 3',3',5',5')-tetramethyl-2'-acetonaphthone

PERFUME PROPERTIES

Yeasty, valerian-like

STRUCTURE OF COMPOUND

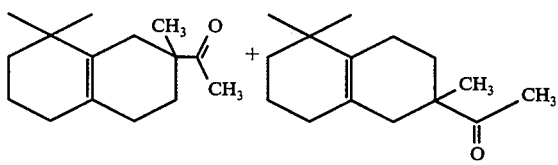

NAME

1',2',3',4',5',6',7',8'-octahydro-2',8',8'(and 2',5',5')-trimethyl-2'-acetonaphthone

PERFUME PROPERTIES

Fruity, woody, pineapple-like

STRUCTURE OF COMPOUND

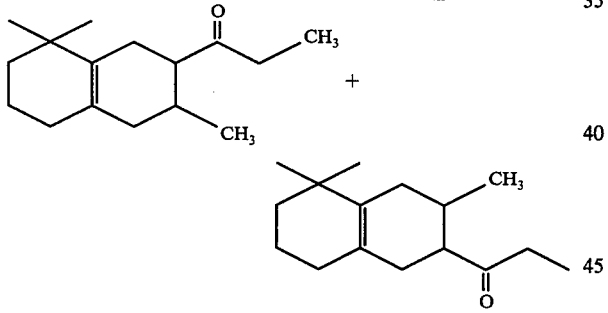

NAME

1',2',3',4',5',6',7',8'-octahydro-3',5',5'(and 3',8',8')-trimethyl-2'-propionaphthone

PERFUME PROPERTIES

Fruity, woody, pineapple-like and ionone like

STRUCTURE OF COMPOUND

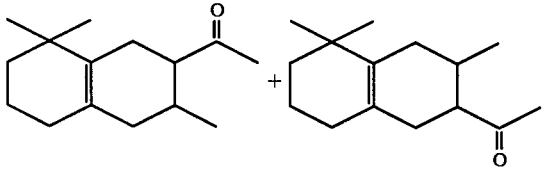

NAME

1',2',3',4',5',6',7',8'-octahydro-3',5',5'-(and 3',8',8')-trimethyl-2'-acetonaphthone

PERFUME PROPERTIES

Low keyed woody, fruity

In addition to the above-mentioned British patent, the above stated sequence of:

1. Diels-Alder Reaction to form Diels-Adler adducts followed by
2. Cyclization of the Diels-Alder adducts is disclosed in detail by Ohloff Ann. 606,100 (1957).

Further, cyclization reactions of Diels-Alder adducts of myrcene and a dienophile are set forth in U.S. Pat. No. 3,076,022. This patent discloses interalia, preparation of the thermal Diels-Alder adduct of myrcene and methyl isopropenyl ketone and subsequent acid cyclization to a product said to possess "an intense ambergris-like note". Repetition of the process as disclosed gave rise to a product possessing fruity, woody, pineapple notes rather than an ambergris-like note.

Ohloff [Chemistry of Odoriferous and Flavoring Substances] pp. 185-240 (at page 192) Fortschritte und der Chemischen Forschung Vol. 12, Part 2, 1969, discloses a compound having the structure:

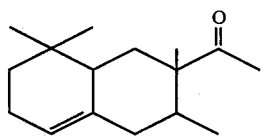

Ohloff indicates that materials of this nature have "resiny odors" like olibanum, with amber type undertones.

However, none of the prior art substituted acetonaphthone compounds possess aromas having sweet woody, vetiver, citrusy, musky, woody/peppery, woody/leathery, hay and green nuances and/or woody fragrance notes of the compounds of our invention.

2-Acetyl-3,4,4a,5,6,7-hexahydro-4a,8-dimethylnaphthalene having the structure:

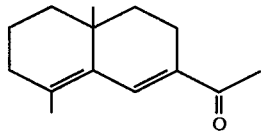

has been determined to occur naturally in vetiver oil. It has a sweet, woody, musky and herbal aroma, from a perfumery standpoint, and a musky, oriental, woody, vetiver aroma profile and a musky, oriental, woody, vetiver, astringent flavor character, having potential uses in blueberry and pear flavors. Although having similar functional groups of the compound of the instant invention, the structure and fragrance profiles are different in kind from the mixtures and isomers of the instant invention.

U.S. Pat. No. 3,845,135, issued on Oct. 29, 1974 is directed to the manufacture of beta ionones but erroneously sets forth a structure at column 1, line 65 thereof as follows:

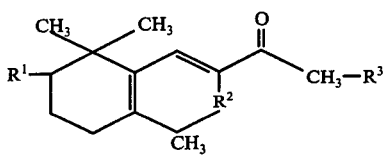

Obviously a printing error occurred showing a bond between the group "R²" and a methyl group.

Other acetyl hexahydro naphthalenes are known, but the structures of such compounds are different in kind from those of the instant invention. Thus, an article by Watt and Corey in Tetrahedron Letters, #46, pages 4651–4654, 1972, discloses compounds having the structures:

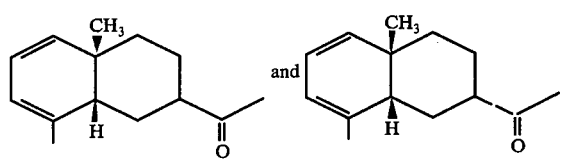

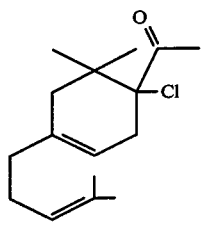

Figure 2:
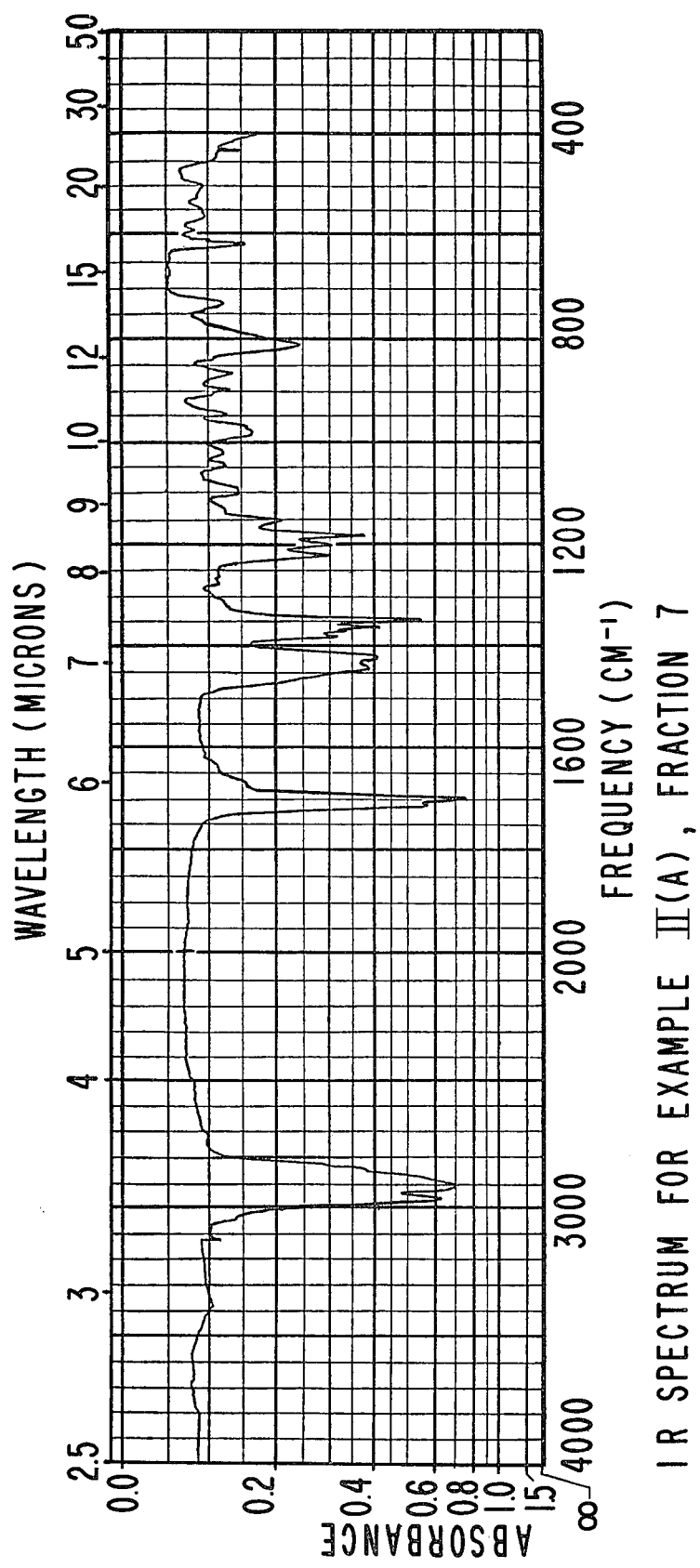

FIG. 2 represents the Infrared spectrum for fraction 7 of Example II (A), which consists of a compound having the structure:

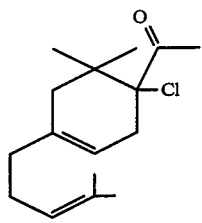

Figure 3:
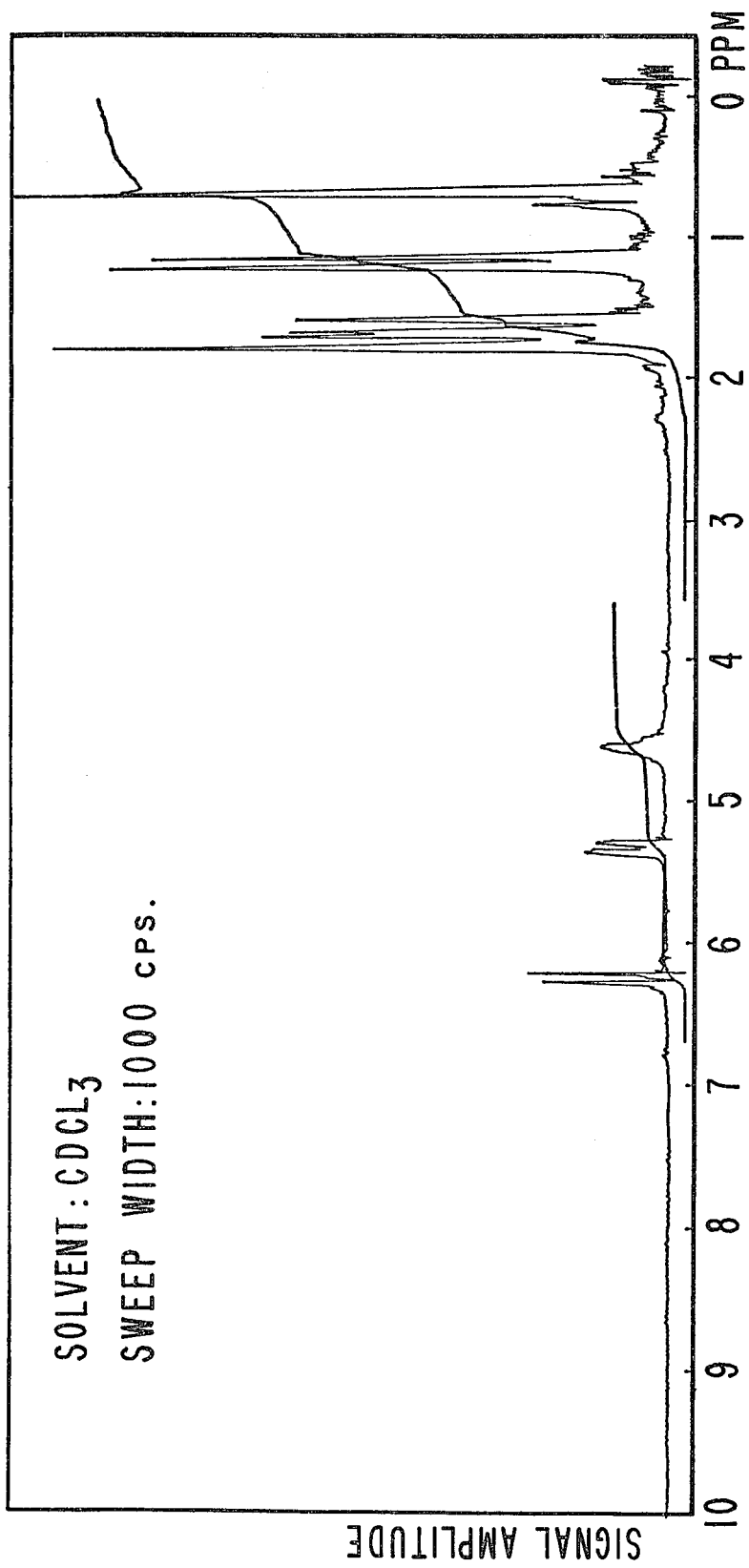

FIG. 3 represents the NMR spectrum for the compound produced according to Example II (B) which has the structure:

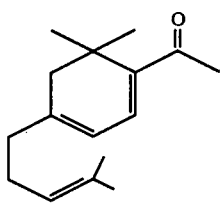

FIG. 4 represents the Infrared spectrum for the compound produced according to Example II (B) which has the structure:

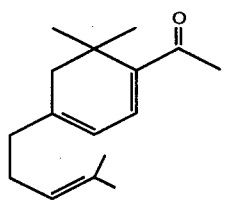

Figure 4A:
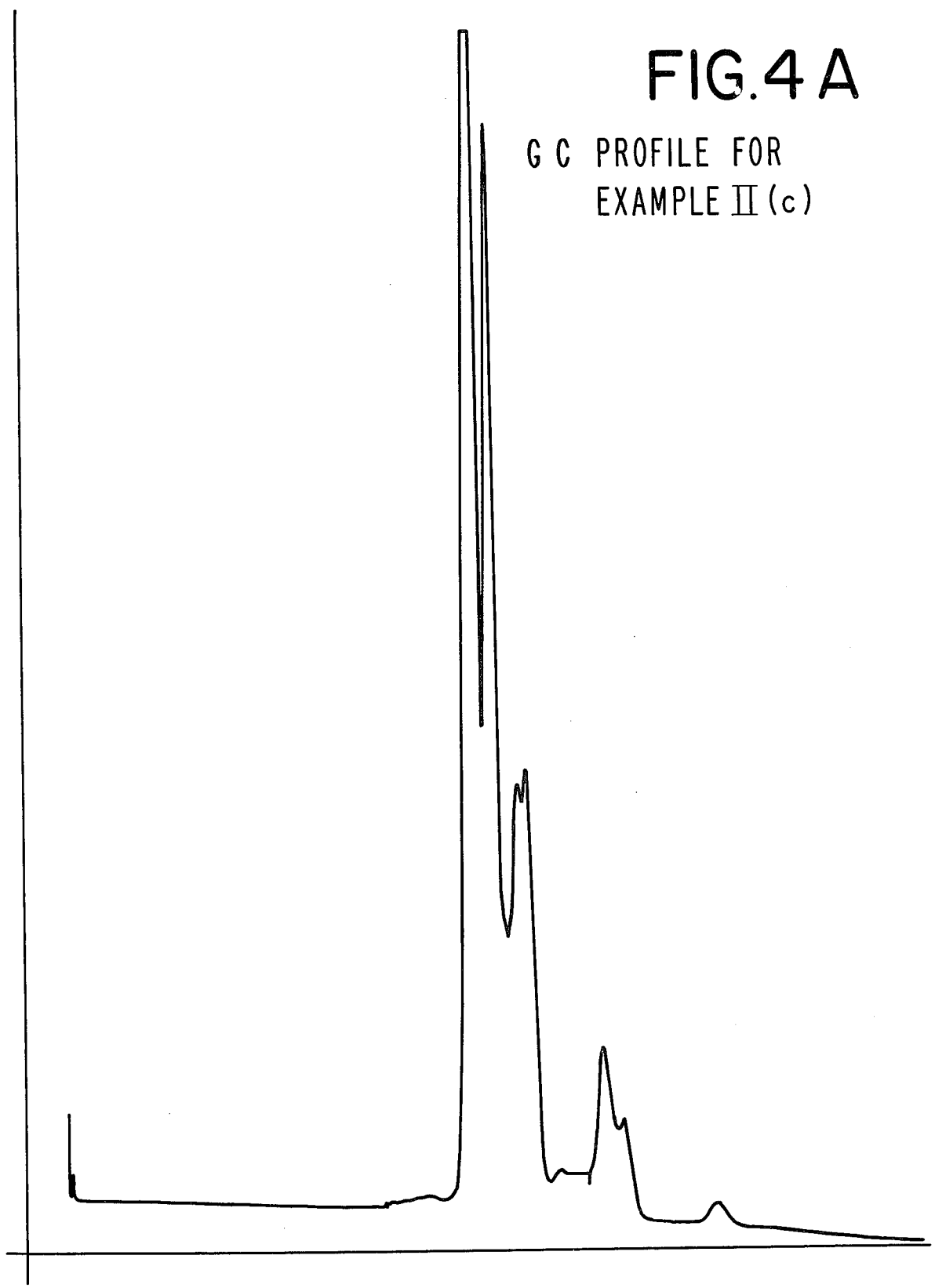

FIG. 4A represents the GC profile for the reaction product produced according to Example II-C.

FIG. 5 represents the NMR spectrum for the TLC trapping identified as "peak 1" produced according to Example II-C and which consists essentially of a compound having the structure:

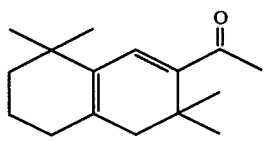

Figure 6:
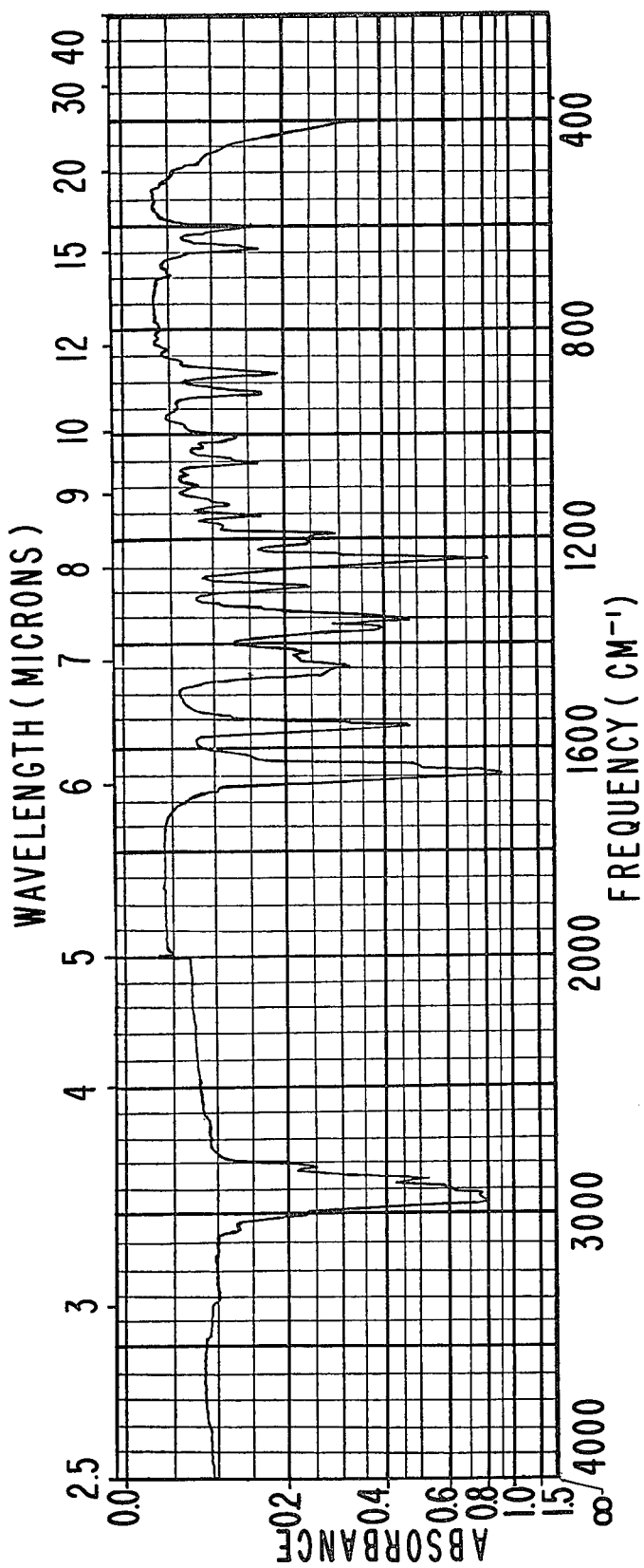

FIG. 6 represents the Infrared spectrum for the GLC trapping identified as "peak 1" produced according to Example II (C) and which consists essentially of a compound having the structure:

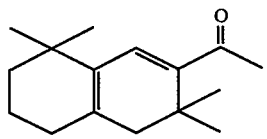

Figure 7:
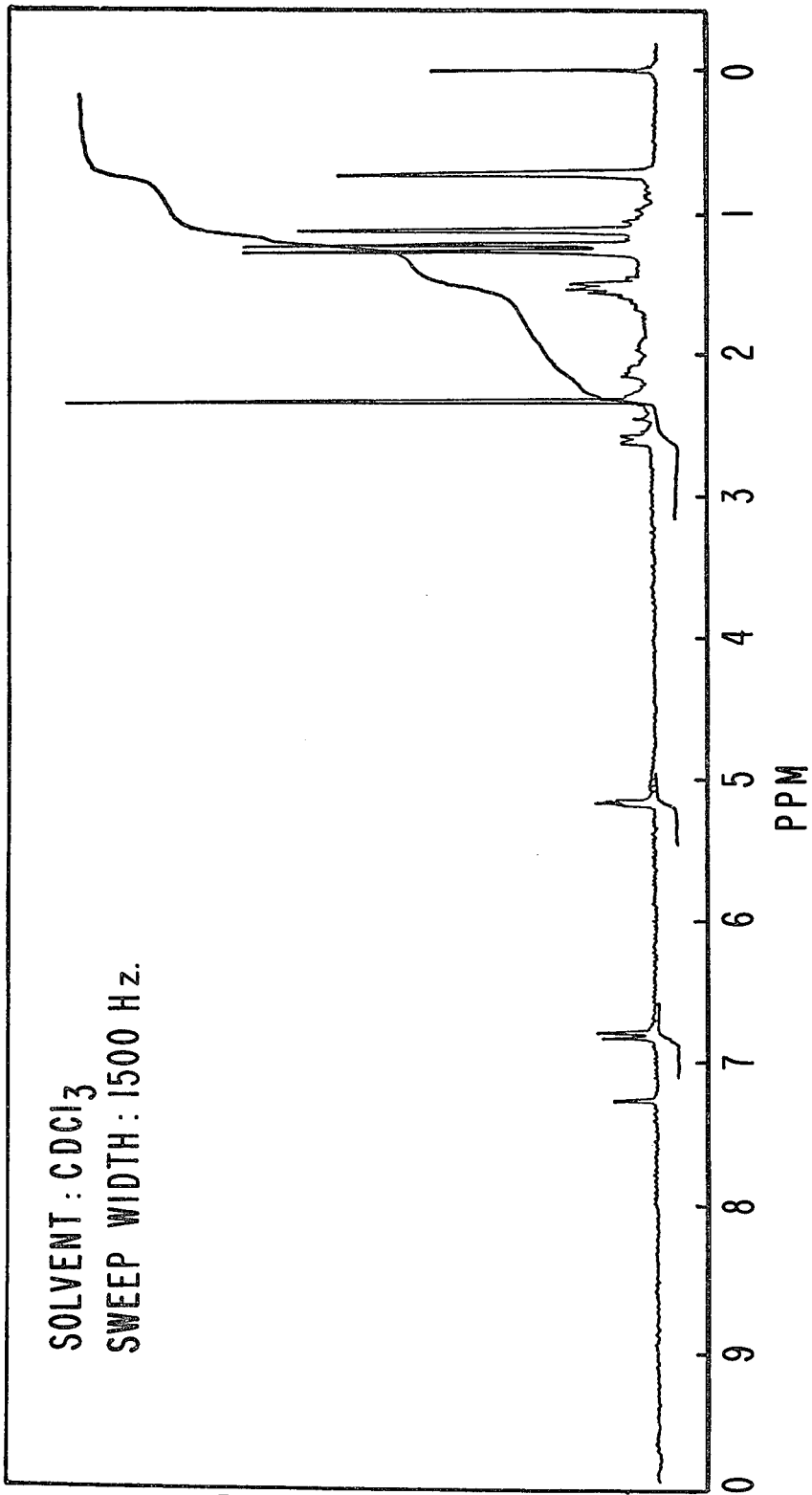

FIG. 7 represents the NMR spectrum for the GLC trapping of Example II (C) identified as "peak 2" and which consists of the novel isomer having the structure:

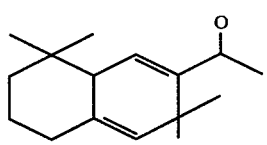

Figure 8:
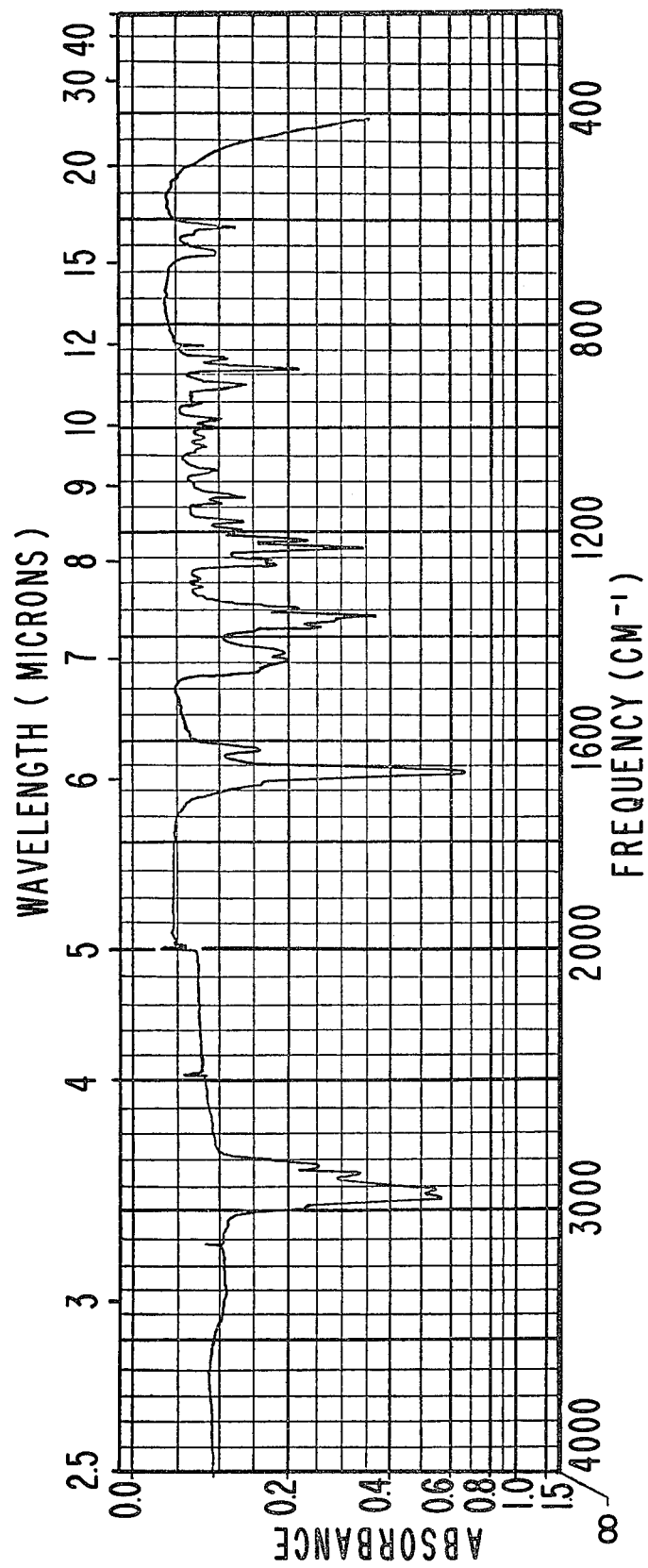

FIG. 8 represents the Infrared spectrum for the GLC trapping of Example II (C) identified as "peak 2" and which consists of a compound having the structure:

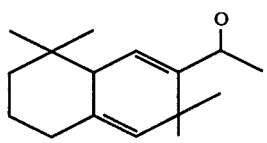

Figure 9:
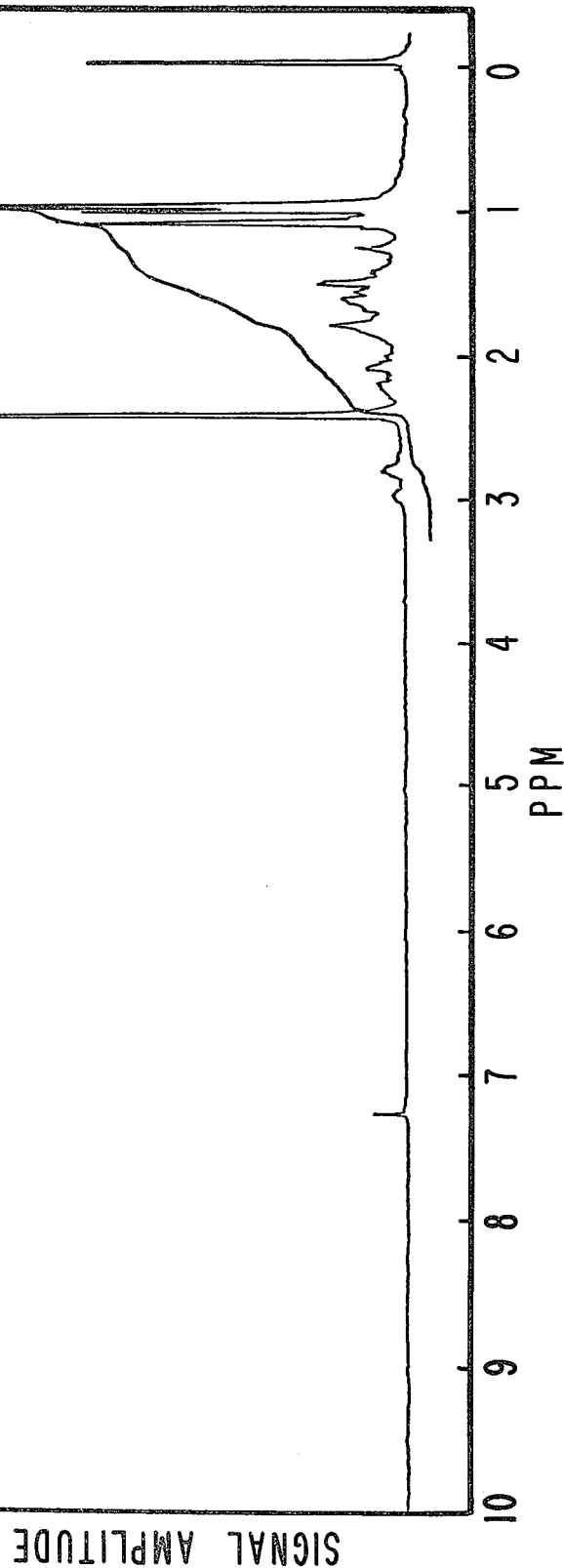

FIG. 9 represents the NMR spectrum of the chlorinated acetyl octahydro naphthalene derivative produced according to Example III (A) having the structure:

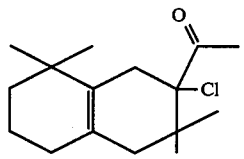

Figure 10:
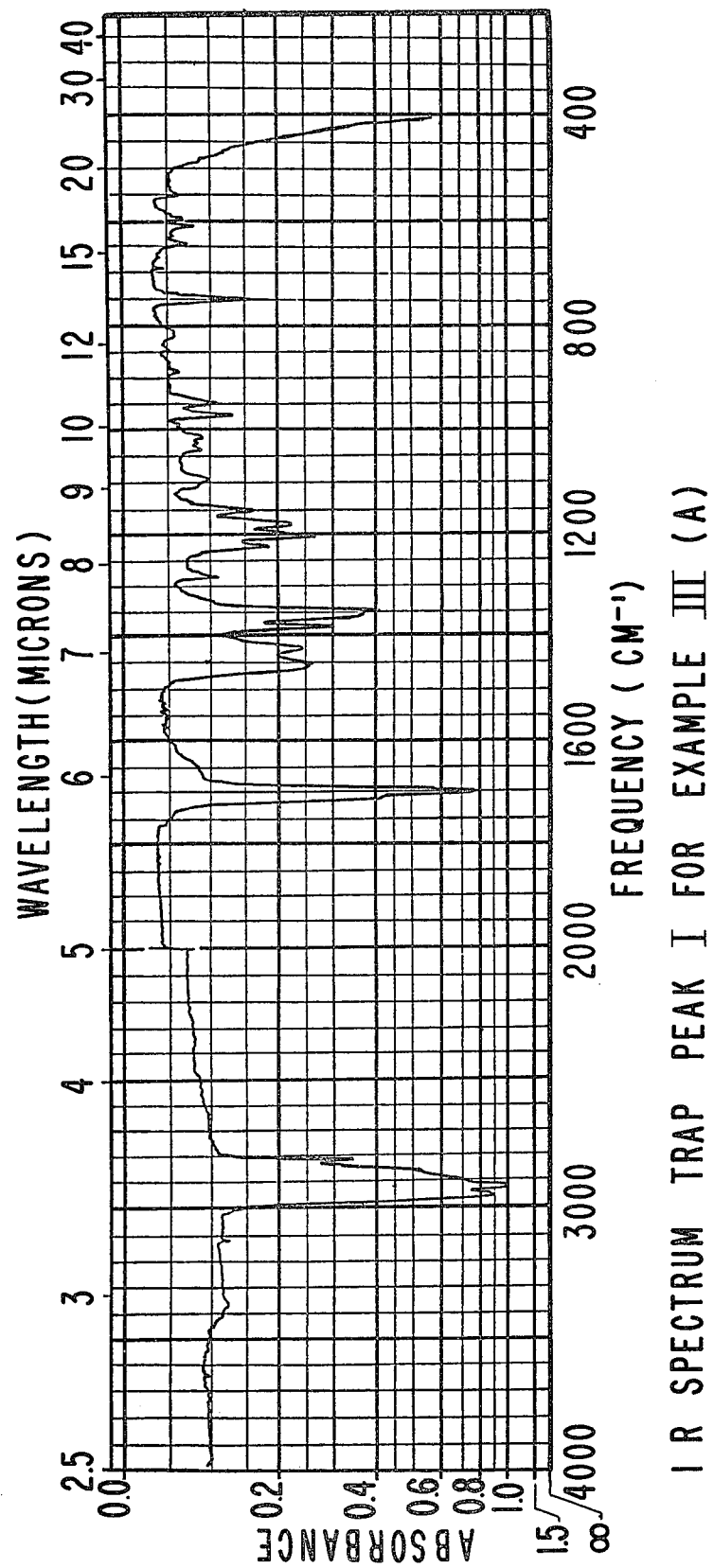

FIG. 10 represents the Infrared spectrum for the compound produced according to Example III (A) which is a chlorinated acetyl octahydro naphthalene derivative having the structure:

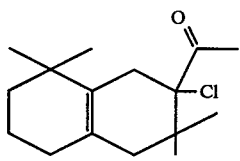

FIG. 11 represents the NMR spectrum for 2-acetyl-3,4,4a,5,6,7-hexahydro-4a,8-dimethylnaphthalene produced according to Example XI and which was isolated from vetiver oil.

FIG. 12 represents the Infrared spectrum for 2-acetyl-3,4,4a,5,6,7-hexahydro-4a,8-dimethylnaphthalene produced according to Example XI and which was isolated from vetiver oil.

THE INVENTION

This invention relates to a genus of substituted hexahydro acetonaphthones having the generic structure:

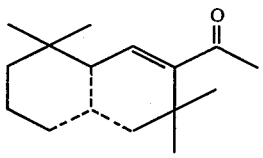

wherein one of the dashed lines is a carbon-carbon double bond and each of the other of the dashed lines is a carbon-carbon single bond as individual compounds and as mixtures. Such compounds are useful as fragrance ingredients for perfumes and perfumed articles including soaps, detergents, cosmetic powders and colognes. More particularly, these compounds have aromas with sweet woody, citrusy, vetiver-like, musky, woody/peppery, woody/leathery, hay and green nuances and/or woody fragrance notes.

The mixtures and isomers of our invention, including the novel isomer having the structure:

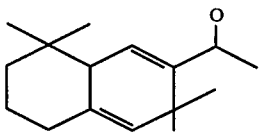

as well as the known individual isomeric component of said mixtures, are produced by first forming 3-chloromesityl oxide from chlorine and mesityl oxide and then reacting the 3-chloromesityl oxide with myrcene via a Diels-Alder reaction thereby forming a chlorine containing Diels-Alder adduct. The chlorine containing Diels-Alder adduct may then either:

(i) be dehydrochlorinated to form an acetyl conjugated cyclohexadiene which may be cyclized to form a mixture of compounds represented by the structure:

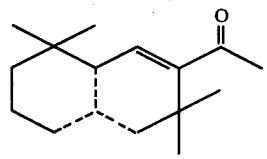

wherein one of the dashed lines is a carbon-carbon double bond and each of the other of the dashed lines is a carbon-carbon single bond; or (ii) it may first be cyclized to form an acetyl chlorinated octahydronaphthalene which may then be dehydrochlorinated to form a composition containing a substantial quantity of the known isomer having the structure:

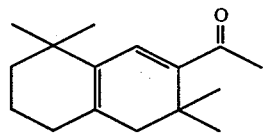

When the mixture of isomers is formed as in method (i), these isomers may, if desired, be separated by means of preparative vapor phase chromatography. As a result of such a separation, the isomer having the structure:

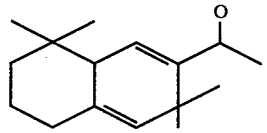

is produced:

The reaction sequence is illustrated as follows:

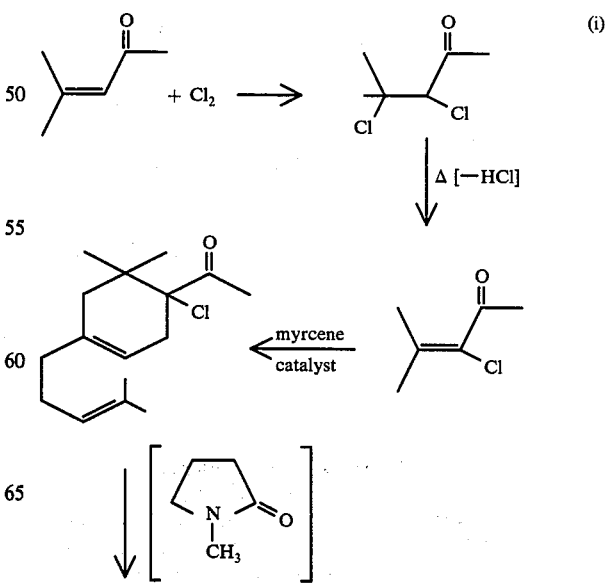

-continued

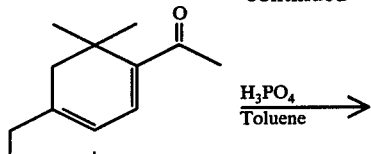

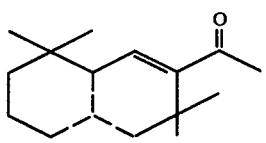

Specifically a mixture of compounds is produced wherein the compounds have the structures:

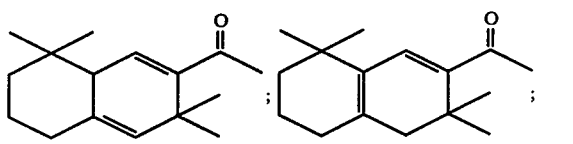

and

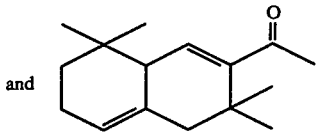

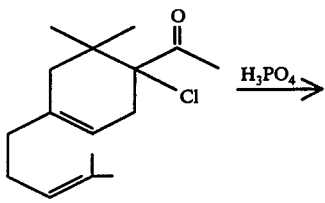

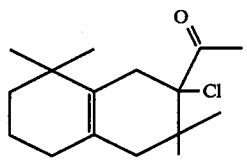

↓ CaCO₃

A composition containing a substantial proportion of the isomer having the structure:

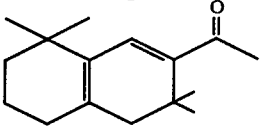

The reaction of chlorine with mesityl oxide results instantly in the formation of a dichloro derivative having the structure:

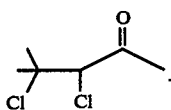

The reaction is carried out in the presence of a solvent such as dimethyl formamide and optionally in the presence of a base such as sodium carbonate or sodium acetate. The mole ratio of chlorine:mesityl oxide is greater than 1 in order to insure completion of reaction. When base is used the mole ratio of base:chlorine is preferably about 1:1. The procedure is related to that of Pauley and Lieck, Ber., 33, 500(1900), but the use of dimethyl formamide represents an improvement over the conditions set forth in the literature.

After the dihalogen compound is formed, it is dehydrohalogenated by means of heating the reaction mixture at a temperature in the range of 90–120° C, preferably 100° C, thereby forming 3-chloromesityl oxide. The reaction of the 3-chloromesityl oxide with myrcene, a Diels-Alder reaction requires the use of one of a specific group of Friedel Crafts type catalysts, namely, stannic chloride or ethyl aluminum dichloride. Aluminum chloride does not give rise to the desired results. The mole ratio of myrcene:3-chloromesityl oxide is preferably near 1:1, although either reagent may be used in excess without harming the yield of the desired chlorine containing Diels-Alder reaction product. Thus, the mole ratio of myrcene:3-chloromesityl oxide may vary from 10:1 up to 1:10 without any variation in the yield of chlorine containing Diels-Alder reaction product. The mole ratio of Friedel Crafts catalyst:3-chloromesityl oxide is preferably between 0.01:1 and 1:1 with the most preferred range being from 0.05:1 to 0.1:1. The Diels-Alder reaction may be carried out at a temperature of between 0° and 100° C with the preferred temperature of reaction being 45°–55° C. The Diels-Alder reaction is preferably carried out in an inert solvent, which may be either benzene, toluene or xylene or a chlorinated hydrocarbon such as methylene dichloride and chloroform.

The dehydrohalogenation of the chlorine containing Diels-Alder reaction product in order to form the acetyl conjugated cyclohexadiene takes place in the presence of a polar, aprotic solvent such as dimethyl formamide, dimethyl acetamide, N-methyl pyrrolidinone, hexamethyl phosphoramide or pyrrole-N-carboxaldehyde. It is also required that this reaction take place in the presence of a base such as calcium carbonate, lithium carbonate, magnesium carbonate, calcium oxide, lithium oxide or magnesium oxide. The temperature of reaction is between 120°–250° C, with a preferred temperature range of 150°–195° C. The mole ratio of base:chlorine containing Diels-Alder adduct is between 0.5:1 and 5:1, with a range of 0.5:1 up to 1:1 being preferred.

Similar conditions are effective for dehydrohalogenation of the chlorinated acetyl octahydronaphthalene derivative having the structure:

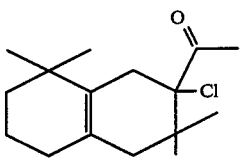

in order to form a composition containing a substantial quantity of the isomer having the structure:

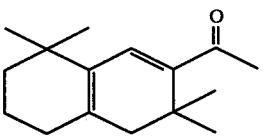

The cyclization reactions for:

(i) cyclizing the chlorine containing Diels-Alder adduct having the structure:

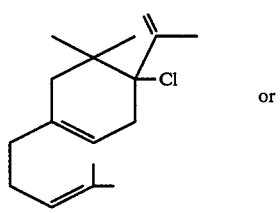

or (ii) cyclizing the acetyl conjugated cyclohexadiene having the structure:

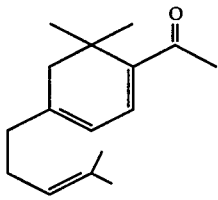

are similar. The cyclization reactions are accomplished by heating the compound to be cyclized preferably with a mixture of an acid such as phosphoric acid, diluted sulfuric acid, boron trifluoride or boron trifluoride etherate in the presence of a solvent. The amount of acid cyclization agent may vary from 10 up to 100 weight percent based on the weight of the compound to be cyclized. Preferably, the weight percent of acid depends upon the particular acid used. For example, when using phosphoric acid, the weight percent should be between 40 and 100 weight percent. Preferably, an inert solvent having a boiling point at or about the desired reaction temperature is used in the cyclization reaction. The reaction temperature may be anywhere between 30° C and the reflux temperature of the reaction mixture. The preferred reaction temperature range is between 40° and 60° C for reaction (ii) and between 70° and 100° C for reaction (i) and toluene is the preferred solvent. The quantity of solvent used in the cyclization reaction may vary from 0 weight percent up to 100 weight percent based on the amount of compound being cyclized. It is preferred to use approximately 25 to 50 weight percent of solvent. In the cyclization reaction, the order of mixing reagents and solvents is not critical.

When a mixture of isomers is prepared having the generic formula:

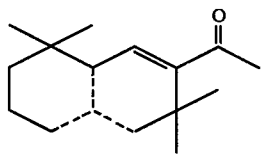

wherein one of the dashed lines is a carbon-carbon double bond and each of the other of the dashed lines is a carbon-carbon single bond, such mixtures can be used "as is" or it may be further purified by using fractional distillation techniques, gas chromatography techniques, and/or oximation, followed by recovery of the purified product from the oxime.

One or more of the hexahydrotetramethyl acetonaphthone derivatives of our invention (including the novel isomer having the structure:

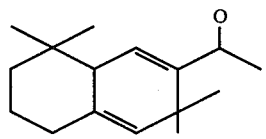

and one or more auxiliary perfume ingredients, including, for example, alcohols, aldehydes, ketones, terpenic hydrocarbons, nitriles, esters, lactones, natural essential oils and synthetic essential oils, may be admixed so that the combined odors of the individual components produce a pleasant and desired fragrance, particularly and preferably in vetiver fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, one or more hexahydrotetramethyl acetonaphthone derivative(s) of our invention can be used to alter, modify or enhance the aroma characteristics of a perfume composition, for example, by utilizing or moderating the olfactory reaction contributed by another ingredient in the composition.

The amount of hexahydrotetramethyl acetonaphthone derivative(s) of our invention which will be effective in perfume compositions as well as in perfumed articles and colognes depends on many factors, including the other ingredients, their amounts and the effects which are desired. It has been found that perfume compositions containing as little as 0.01% of hexahydrotetramethyl acetonaphthone derivative(s) or even less (e.g., 0.005%) can be used to impart a vetiver aroma with sweet woody, citrusy, musky, woody/peppery, woody/leathery, hay and green nuances to soaps, cosmetics, detergents, powders and colognes. The amount employed can range up to 70% of the fragrance components and will depend on considerations of cost, nature of the end product, the effect desired on the finished product and the particular fragrance sought.

The hexahydrotetramethyl acetonaphthone derivative(s) of our invention are useful [taken alone or together with other ingredients in perfume compositions] as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens powders, such as talcs, dusting powders, face powders and the like. When used as (an) olfactory component(s) as little as 1% of hexahydrotetramethyl acetonaphthone derivative(s) will suffice to impart an intense aroma with sweet woody, vetiver, citrusy, musky, woody/peppery, woody/leathery, hay and green nuances to vetiver formulations. Although, generally, no more than 60% of hexahydrotetramethyl acetonaphthone derivative(s), based on the ultimate end product, is required in the perfume composition, amounts of hexahydrotetramethyl acetonaphthone derivative of up to 95% may be used in such perfume composition.

In addition, the perfume composition or fragrance composition of our invention can contain a vehicle, or carrier for the hexahydrotetramethyl acetonaphthone derivative(s). The vehicle can be liquid such as a non-toxic alcohol, a non-toxic glycol, or the like. The carrier can also be an absorbent solid, such as a gum (e.g., gum arabic) or components for encapsulating the composition (such as gelatin).

It will thus be apparent that the hexahydrotetramethyl acetonaphthone derivative(s) of our invention can be utilized to alter, modify or enhance sensory properties, particularly organoleptic properties, such as flavor(s) and/or fragrance(s) of a wide variety of consumable materials.

The following examples serve to illustrate our invention and the invention is to be considered restricted thereto only as indicated in the appended claims.

All parts and percentages given herein are by weight unless otherwise specified.

EXAMPLE I (A)

PREPARATION OF 3-CHLOROMESITYL OXIDE

Reaction:

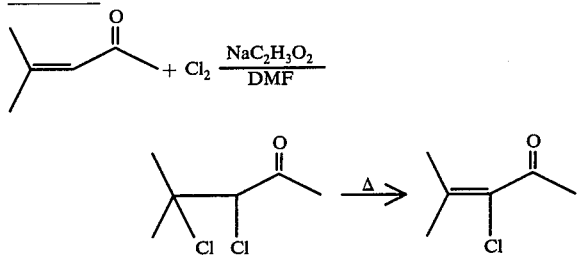

Procedure

Into a 12 liter reaction flask equipped with stirrer, condenser, thermometer and gas addition tube, 1963 g (20.0 moles) mesityl oxide, 2050 g (25.0 moles) of sodium acetate and 2000 ml dimethyl formamide are placed. The contents of the flask are cooled to 0° C. At a rapid rate over a 3½ hour period, while maintaining the reaction mass at 0° C, 888 g (25.0 moles) chlorine is added to the reaction mass. The mixture is then heated to 100° C for a period of 2 hours. Sufficient quantities of water are added to the reaction mass to cause it to separate into two phases. The organic phase is washed with two 2000 cc portions of water, and then dried over anhydrous magnesium sulfate, filtered and distilled through a 12 inch × 1½ inch stone packed column yielding 1740 grams of product, b.p. 68°–69° C (45 mm Hg).

EXAMPLE I (B)

PREPARATION OF 3-CHLOROMESITYL OXIDE

A 22 liter three necked reaction flask equipped with stirrer, thermometer, cooling bath and gas inlet tube is charged with 4900 grams of mesityl oxide and 2500 ml dimethylformamide. The mixture is stirred at 0°–5° C, as 4438 grams of chlorine is added over a 5 hour period. Nitrogen is then passed through the mixture as it is heated to 100° C and held at that temperature for 3 hours. The cooled reaction mass is washed with three volumes of water (methylene chloride is added to aid in separation of the layers). The organic phase is then distilled though a 2′ × 1½ inch column packed with porcelain saddles to give 3231 grams product, b.p. 70°–80° C (50 mm Hg).

EXAMPLE II (A)

DIELS-ALDER REACTION OF MYRCENS WITH 3-CHLOROMESITYL OXIDE

Reaction:

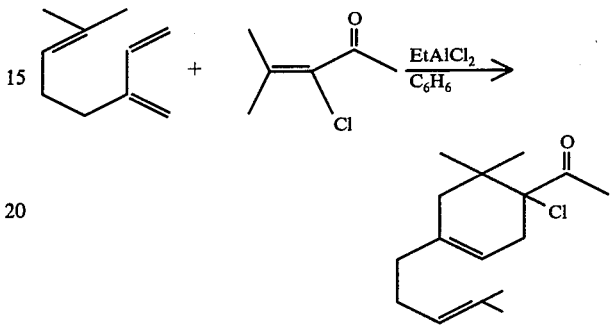

Procedure

Into a 500 cc reaction flask equipped with stirrer, themometer, addition funnel, heating mantle and nitrogen blanket is placed 13 g of 25% ethyl aluminum dichloride in heptane (0.025 moles) and a solution of 35 g (0.25 moles) of 3-chloromesityl oxide in 50 ml anhydrous benzene. While maintaining the resulting mixture at a temperature of 4° C, over a period of 30 minutes, a solution of 53 g of 85% myrcene (0.30 moles) in 50 ml benzene is added. The reaction mass is then allowed to warm to room temperature and then stirred at a temperature of between 25° and 45° C for a period of 5 hours. 250 ml water and 300 ml diethyl ether is then added to the reaction mass. The organic phase is separated, washed with water, dried and stripped of solvent. The resulting oil is distilled through a micro Vigreux column to give 47.0 g product, b.p. 112°–123° C (0.8 mm Hg).

Fraction 7, b.p. 120°–123° C (0.8 mm Hg), is analyzed using NMR and Infrared analyses.

Figure 1:
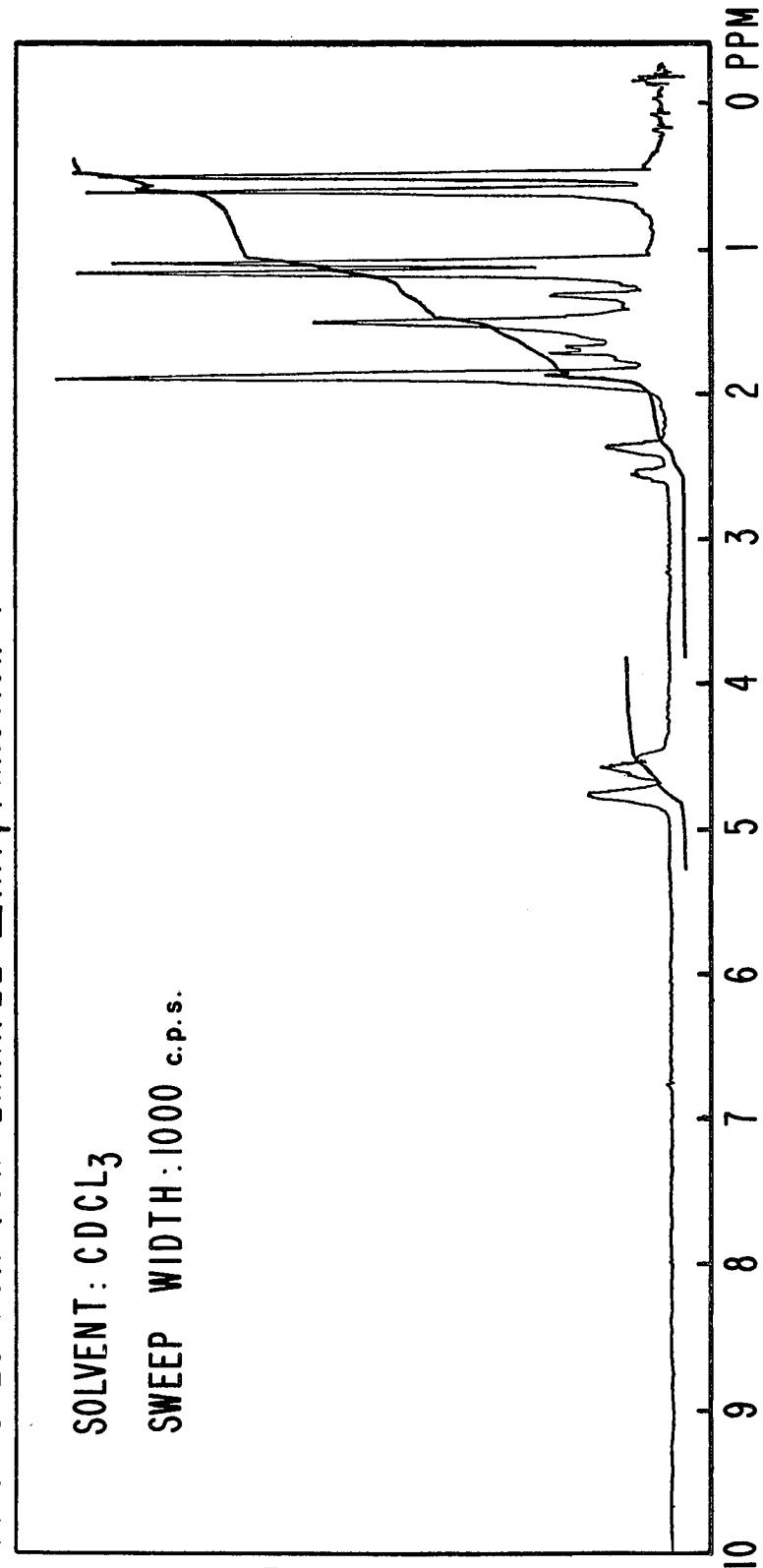
FIG. 1 illustrates the NMR spectrum for fraction 7 produced according to Example II (A), which consists of a compound having the structure.

The NMR sprectrum is set forth in FIG. 1. The Infrared spectrum is set forth in FIG. 2.

The NMR spectrum is as follows:

| δ, ppm | Assignment | |
| --- | --- | --- |
| 0.97–1.10 | gem dimethyl protons | 6H |
| 1.60 | $\begin{array}{c}CH_3\\ =C\\ CH_3\end{array}$ | 6M |
| 2.46–1.82 | —CH$_2$— | 8H |
| 2.36 | $\begin{array}{c}O\\ \parallel\\ CH_3—C—\end{array}$ | 3H |
| 5.08 | $\begin{array}{c}Me\\ HC=C\\ Me\end{array}$ | 1H |
| 5.27 | "cyclic" olefinic proton | 1H |

The Infrared spectrum contains the following bands: 810, 1150, 1180, 1200, 1220, 1350, 1365, 1425, 1445, 1700, 1700, 2920, 2970 cm$^{-1}$.

EXAMPLE II (B)

DEHYDROHALOGENATION OF DIELS-ALDER ADDUCT

Reaction:

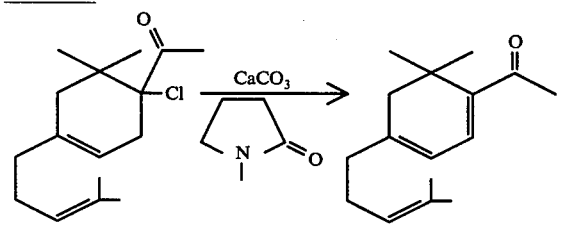

Procedure

Into a 250 cc reaction flask equipped with stirrer, thermometer, reflux condenser and heating mantle is placed 48 g (0.22 moles) of the Diels-Alder adduct produced according to Example II (A), 125 ml N-methylpyrrolidinone and 35 g calcium carbonate. The reaction mass is heated and maintained at 150°–180° C for a period of 1 hour. The reaction mass is then cooled to room temperature, after which time it is filtered and the solids washed with diethyl ether. The solution is washed with water and the aqueous phase is extracted with diethyl ether. The ether extracts are bulked, dried over anhydrous magnesium sulfate, stripped of solvent and distilled through a micro Vigreux column to give 28.0 g product, b.p. 122°–128° C (1.0 mm Hg).

NMR and Infrared analysis confirm that the resulting product has the structure:

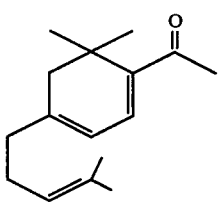

The NMR spectrum is set forth in FIG. 3. The Infrared spectrum is set forth in FIG. 4.

The NMR spectrum is as follows:

| δ, ppm | Assignment | |
|---|---|---|
| 1.14 | gem dimethyl protons | 6H |
| 1.62 | =C$\diagdown$CH$_3$ $\diagup$CH$_3$ | 6H |
| 2.16–2.06 | =C—CH$_2$— | 6H |
| 2.24 | $\underset{\underset{\displaystyle CH_3-C-C=C}{\|}}{O}$ | 3H |
| 5.1 | olefinic proton | 1H |
| 5.80 | | |
| 6.72 | C=CH—CH=C—$\underset{\|}{\overset{O}{\|}}$C— | 2H |

The Infrared spectrum contains the following bands: 1205, 1245, 1260, 1350, 1360, 1370, 1380, 1450, 1560, 1635, 1655, 2860, 2920, 2950 cm$^{-1}$.

EXAMPLE II (C)

CYCLIZATION OF ACETYL CONJUGATED CYCLOHEXADIENE DERIVATIVE

Reaction:

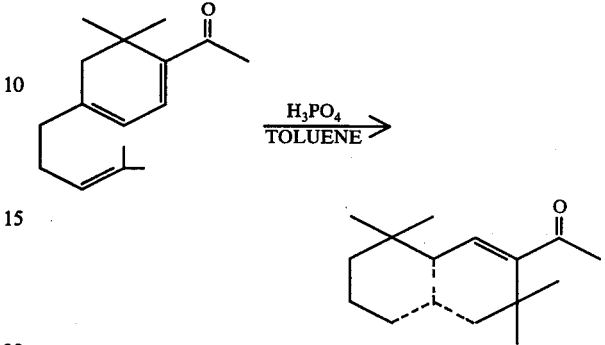

Procedure

Into a 100 ml reaction flask equipped with stirrer, reflux condenser, thermometer and heating mantle are placed 25 g of the acetyl conjugated cyclohexadiene derivative produced according to Example II (B), 25 g 85% phosphoric acid and 10 g of toluene.

The reaction mass is stirred at a temperature of 25°–35° C for a period of 2 hours, after which time it is heated at 50°–65° C over a period of 1½ hours. At the end of this period of time, the reaction mass is cooled to room temperature and two volumes of water are added. The aqueous phase is separated from the organic phase and then extracted with an equal volume of toluene. The combined organic layers are washed with water, aqueous sodium bicarbonate and then washed neutral with water. The organic phase is then stripped of solvent (crude weight: 30 g) and distilled on a 4 inch micro Vigreux column yielding 19.0 g material, b.p. 126°–145° C (0.8–0.9 mm Hg).

Fraction 4 is confirmed to be a mixture of compounds having the structure:

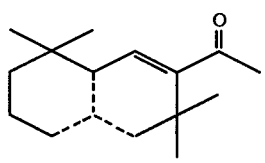

wherein one of the dashed lines is a carbon-carbon double bond and each of the other of the dashed lines is a carbon-carbon single bond by NMR and Infrared analyses.

The GC profile for fraction 4 is set forth in FIG. 4A.

The components of fraction 4 are separated using preparative GLC (6′ × ¼ inch Carbowax 20M column). Peak 1 is confirmed by NMR and Infrared analyses. The mixture contains the following compounds:

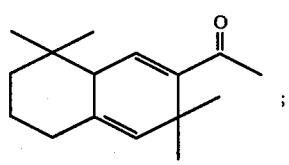
;

-continued

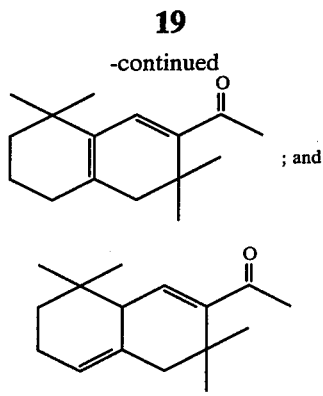
; and

Peak 2 is confirmed by NMR and Infrared analyses to have the structure:

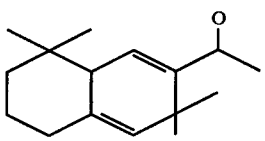

Peak 1 is described as having a woody, musky note and peak 2 is described as having a woody, peppery note. The entire mixture in fraction 4 has a sweet, woody, herbal, vetiver aroma with a citrus, vetivone undertone. Peak 3 has a woody, leathery, "cymeme" note.

FIG. 5 illustrates the NMR spectrum for peak 1. FIG. 6 illustrates the Infrared spectrum for peak 1.

The NMR analysis for peak 1 is as follows:

| $\delta$, ppm | Assignment | |
|---|---|---|
| 1.04 | gem dimethyl protons | 6H |
| 1.12 | gem dimethyl protons | 6H |
| 1.56 | —CH$_2$— | 4H |
| 1.98 | =C—CH$_2$— | 4H |
| 2.30 | CH$_3$—C—$\overset{O}{\|}$ | 3H |
| 6.80 | olefinic proton | 1H |

The Infrared spectrum of peak 1 contains the following bands:

1195, 1240, 1355, 1370, 1450, 1560, 1640, 1655, 2860, 2900, 2920, 2950 cm$^{-1}$.

FIG. 7 illustrates the NMR spectrum for peak 2. FIG. 8 illustrates the Infrared spectrum for peak 2.

The NMR analysis for peak 2 is as follows:

| $\delta$, ppm | Assignment | |
|---|---|---|
| 0.72 | | |
| 1.10 | | |
| 1.22 | gem dimethyl protons | 12H |
| 1.26 | | |
| 1.30–1.04 | | |
| 1.50 | —CH$_2$— | 4H |
| 2.00 | =C—CH$_2$ | 2H |
| 2.32 | CH$_3$—C—C=C—$\overset{O}{\|}$ | 3H |
| 2.60 | HC—C=C—C—$\overset{O}{\|}$ | 1H |
| 5.16 | olefinic proton | 1H |
| 6.78 | HC—C=C—C—$\overset{O}{\|}$ | 1H |

The Infrared spectrum of peak 2 contains the following bands:

885, 1210, 1230, 1345, 1410, 1710, 2830, 2860, 2920, 2950 cm$^{-1}$.

EXAMPLE III (A)

PREPARATION OF CHLORINATED ACETYL OCTAHYDRO NAPHTHALENE DERIVATIVE BY CYCLIZATION OF CHLORINATED DIELS-ALDER ADDUCT

Reactions:

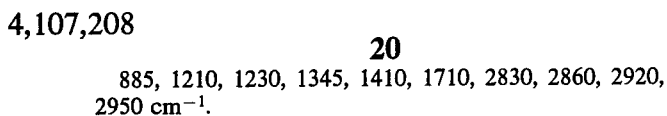

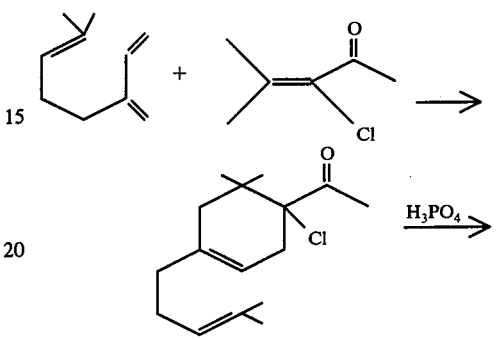 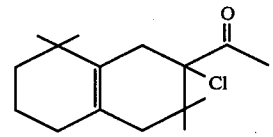

Procedure

Into a 3 liter reaction flask equipped with stirrer, thermometer, condenser, dropping funnel and nitrogen inlet is placed 202 g of toluene and 52.0 g (0.40 moles) of ethyl aluminum dichloride. 53.0 g (4.0 moles) of alpha-chloromesityl oxide, prepared according to Example I (A), is then added and the resulting solution is heated to 45° C. While stirring the reaction mass at 45° C, 640 g of 85% myrcene is added dropwise over a period of 1 hour. The reaction mass is then stirred at 45° C for a period of 2 hours and then monitored by GLC (conditions: SF 96 column, programmed at 100°–220° C at 8° C per minute). Another 100 g of 85% myrcene (total myrcene: 740 g; 5.44 moles) is added to the reaction mass and the temperature of the reaction mass is raised to 60° C and maintained at that temperature for 2½ hours.

1270 g (12.9 moles) of phosphoric acid is then added to the reaction mass over a 30 minute period, while maintaining the temperature at 25°–30° C. The reaction mass is stirred at 60° C for 8 hours and then cooled to room temperature.

1 Liter of water is added to the reaction mass and the resulting mixture is stirred for 15 minutes. The reaction mass is then extracted with two 500 cc portions of diethyl ether and the ether extracts are combined with two 300 cc portions of saturated sodium bicarbonate, dried over anhydrous sodium sulfate and distilled without fractionation to yield 600 g of product, which is confirmed by NMR and Infrared analyses to have the structure:

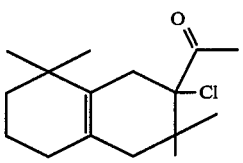

FIG. 9 illustrates the NMR spectrum for this cholorinated acetyl octahydronaphthalene derivative. FIG. 10 illustrates the Infrared spectrum for said chlorinated acetyl octahydronaphthalene derivative.

The NMR analysis is as follows:

| δ, ppm | Assignment | |
|---|---|---|
| 0.98 | gem dimethyl protons | 6H |
| 1.00, 1.09 | gem dimethyl protons | 6H |
| 2.24–1.26 | —$CH_2$— | 8H |
| 2.42 | $CH_3$—$\overset{O}{\underset{\|}{C}}$— | 3H |

The Infrared spectrum contains the following bands: 1180, 1205, 1350, 1375, 1420, 1450, 1700, 2920, 2960 $cm^{-1}$.

EXAMPLE III (B)

PREPARATION OF HEXAHYDRO ACETONAPHTHONE DERIVATIVE FROM CHLORINATED ACETYL OCTAHYDRONAPHTHALENE DERIVATIVE

Reaction:

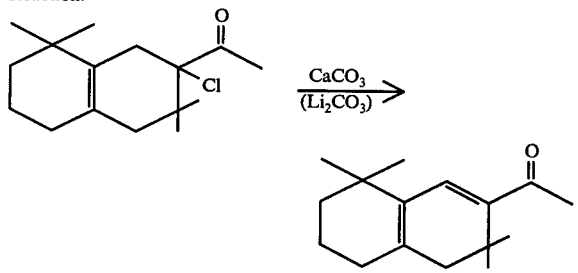

Procedure

The 600 g of the chlorinated acetyl octahydronaphthalene derivative, produced in Example III (A), is placed in a 1 liter reaction flask along with 500 cc dimethyl formamide and 109.5 g calcium carbonate. The reaction mass is then refluxed at 140°–150° C for a period of 8 hours. 27 g lithium carbonate is then added to the solution and refluxing is continued for another 5 hours whereupon GLC analysis indicates completion of the reaction (GLC conditions: 6' × ¼ inch 12% SF 96 column, programmed at 100°–220° C at 8° C per minute).

250 cc water is then added to the reaction mass and the organic layer is separated. The aqueous phase is then extracted with two 200 cc portions of diethyl ether. The extracts are combined with the first organic layer and washed with two 500 cc portions of water, dried over anhydrous sodium sulfate, concentrated and distilled without fractionation.

This material is then re-distilled through a 2' × 1 inch Goodloe packed column to give 152 g product, b.p. 100°–111° C (0.4–0.5 mm Hg).

GLC, NMR and Infrared analyses confirm that the resulting product has the structure:

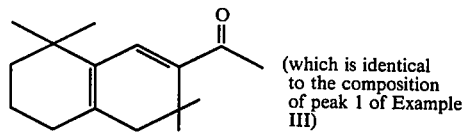

(which is identical to the composition of peak 1 of Example III)

EXAMPLE IV

VETIVER FRAGRANCE

The following mixture is prepared:

| Ingredients | Parts by Weight |
|---|---|
| Hexahydro acetonaphthone derivative prepared according to Example III (B) | 50 |
| Cedrol | 25 |
| Cedrenyl Acetate | 5 |
| Isobutyl Quinoline | 1 |
| Beta Ionone | 2 |
| Caryophyllene | 15 |
| Eugenol | 2 |
| | 100 |

The hexahydro acetonaphthone derivative prepared according to Example III (B) imparts the rich, deep, green, woody note of vetiver to this vetiver fragrance.

EXAMPLE V

VETIVER FRAGRANCE

The following mixture is prepared:

| Ingredients | Parts by Weight |
|---|---|
| Hexahydro acetonaphthone derivative prepared according to Example II (C) | 50 |
| Cedrol | 25 |
| Cedrenyl Acetate | 5 |
| Isobutyl Quinoline | 1 |
| Beta Ionone | 2 |
| caryophyllene | 15 |
| Eugenol | 2 |
| | 100 |

The hexahydro acetonaphthone derivative prepared according to Example II (C) imparts the rich, deep, green, woody note of vetiver to this vetiver fragrance.

EXAMPLE VI

PREPARATION OF A COSMETIC POWDER COMPOSITION

A cosmetic powder is prepared by mixing in a ball mill, 100 g of talcum powder with 0.25 g of the hexahydro acetonaphthone derivative produced according to Example II (C). It has an excellent vetiver aroma with green, sweet woody, citrusy, musky and woody/peppery and woody/leathery nuances.

EXAMPLE VII

PERFUMED LIQUID DETERGENT

Concentrated liquid detergents with deep, green, grapefruit and woody aromas (which detergents are produced from Lysine salt of n-dodecyl benzene sulfonic acid, as more specifically described in U.S. Pat. No. 3,948,818, issued on Apr. 6, 1976) are prepared containing hexahydro acetonaphthone derivative prepared according to Example IV. They are prepared by adding and homogeneously mixing the appropriate quantity of hexahydro acetonaphthone derivative in the liquid detergent. The detergents all possess a deep, green, musky, grapefruit and woody aroma, the intensity increasing with greater concentrations of hexahydro acetonaphthone derivative.

EXAMPLE VIII

PREPARATION OF A COLOGNE AND HANDKERCHIEF PERFUME

Hexahydro acetonaphthone derivative, prepared according to the process of Example IV is incorporated in a cologne at a concentration of 2.5% in 85% aqueous ethanol; and into a handkerchief perfume at a concentration of 20% (in 95% aqueous ethanol). A distinct and definite deep, green, musky, grapefruit and woody aroma is imparted to the cologne and to the handkerchief perfume.

EXAMPLE IX

PREPARATION OF A COLOGNE AND HANDKERCHIEF PERFUME

The composition of Example V is incorporated in a cologne at a concentration of 2.5% in 85% aqueous ethanol; and into a handkerchief perfume at a concentration of 20% (in 95% aqueous ethanol). The use of the hexahydro acetonaphthone derivative in the composition of Example V affords a distinct and definite deep, green, musky, grapefruit and woody aroma to the handkerchief perfume and cologne.

EXAMPLE X

PREPARATION OF SOAP COMPOSITION

One hundred grams of soap chips are mixed with two grams of the composition of Example V until a substantially homogeneous composition is obtained. The perfumed soap composition manifests an excellent vetiver aroma with rich, deep, green, musky and wood notes.

EXAMPLE XI

PREPARATION OF A DETERGENT COMPOSITION

A total of 100 grams of a detergent powder (Lysine salt of n-dodecyl benzene sulfonic acid, as more specifically described in U.S. Pat. No. 3,948,818, issued on Apr. 6, 1976) is mixed with 0.70 grams of the composition of Example V until a substantially homogeneous composition is obtained. This composition has an excellent vetiver aroma with rich, deep, green and woody notes.

EXAMPLE XII

ISOLATION OF 2-ACETYL-3,4,4a,5,6,7-HEXAHYDRO-4a,8-DIMETHYL-NAPHTHALENE

A mixture of 300 g of vetivert oil Haiti is intimately admixed with 450 ml anhydrous methanol, 45 ml glacial acetic acid and 90 g of Girard-P reagent and placed in a 1 liter reaction flask and refluxed for a period of 1 hour at 80° C. The resulting mixture is then poured over a mixture of 1800 g of ice and 27.0 g of aqueous sodium hydroxide solution.

The resulting reaction mass is then placed in a separatory funnel and the aqueous phase is separated from the oil phase. To the aqueous phase is added 450 ml concentrated hydrochloric acid and the mixture is kept at room temperature for 90 minutes. The mixture is extracted three times with ether and the combined extracts are washed with aqueous sodium bicarbonate and saturated brine. The organic phase is dried over MgSO$_4$, concentrated to give 45 g of oil which is then distilled on a spinning band apparatus. A total of 22 fractions are collected. Fraction 12 which boils at 102° C (0.5 mm Hg) weighs 3.9 g. 3.6 g of this fraction are chromatographed over 100 g of silica gel (deactivated with 5% water), eluting with 2% diethyl ether in isopentane. A 0.8 g portion of this material is re-chromatographed over 50 g deactivated silica gel, eluting with 1.5% ether in isopentane. From this twice chromatographed material the major peak is isolated by preparative GLC on a Carbowax column and is shown by NMR, IR and Mass Spectral analyses to have the following structure:

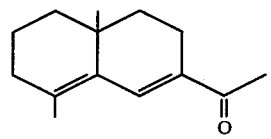

The NMR spectrum of this material is set forth in FIG. 11. The Infrared spectrum is set forth in FIG. 12.

The mass spectrum contains the following ions:

| m/e | = | relative intensity |
|-----|---|--------------------|
| 39  |   | 23  |
| 41  |   | 21  |
| 43  |   | 100 |
| 91  |   | 20  |
| 105 |   | 19  |
| 161 |   | 33  |
| 189 |   | 47  |
| M204 |  | 51  |

EXAMPLE XIII

SYNTHESIS OF 2-ACETYL-3,4,4a,5,6,7-HEXAHYDRO-4a,8-DIMETHYL-NAPHTHALENE

Part A: Synthesis of trans-8,10-dimethyl(9)octal-2-one

Reaction:

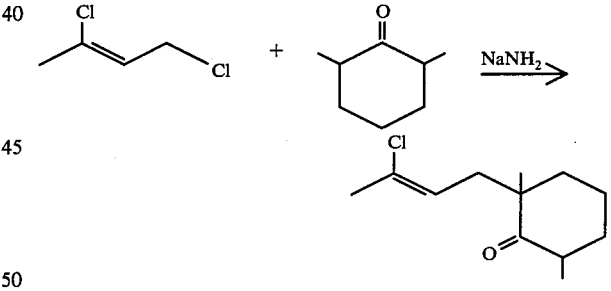

Procedure

Under a nitrogen purge, a mixture of 42 grams sodamide (1.07 moles), 138 grams, 2,6-dimethyl cyclohexanone (1.1 moles) and 750 ml benzene is refluxed for a period of 5 hours. A solution of 126 grams (1 mole) of 1,3-dichloro-butene in 100 ml benzene is added slowly to the above reaction mass which is then refluxed for another 4 hours. The mixture is cooled to room temperature, and then 100 ml aqueous 6 molar hydrochloric acid is added. The reaction mixture is then extracted with five 100 ml portions of diethyl ether and the extracts are combined, dried over anhydrous magnesium sulfate and the solvents evaporated, thereby giving 205 g of crude reaction product. The resulting material is distilled on a 6" silvered column yielding 148.4 g of product, b.p. 75°–78° C (0.1–0.2 mm Hg). The reaction product has the structure:

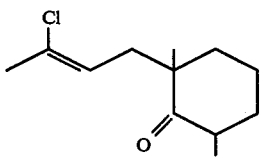

Part B: Production of 2,6-dimethyl-2(3-butynyl)cyclohexanone

Reaction:

 

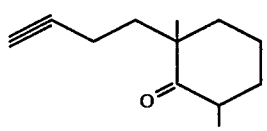

Procedure

Under a nitrogen blanket in a 1 liter reaction flask is placed 39.9 g (1.02 moles) of sodamide in 200 ml toluene. With stirring, 43.8 grams of the 2,6-dimethyl-2(gamma-chlorocrotyl)cyclohexanone produced according to Part A in 200 ml toluene is added to the sodamide mixture and the resulting reaction mass is refluxed at 105°–110° C for a period of 12 hours.

The reaction mass is then cooled to 0°–5° C and 10% aqueous HCl (200 ml) is added and the reaction mass is then stirred for 10 minutes at room temperature. The reaction mass is then extracted with five 100 ml portions of diethyl ether and the ether extracts are combined, dried over anhydrous magnesium sulfate and evaporated yielding 47.0 g of a crude product which is distilled to yield 27.0 g of 2,6-dimethyl-2(3-butynyl)cyclohexanone having the structure:

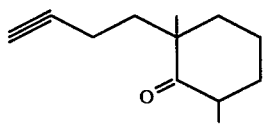

Part C: Production of 2,6-dimethyl-2,3(oxobutyl)cyclohexanone

Reaction:

 

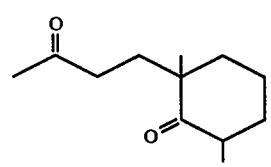

Procedure

A mixture of 27 g of 2,6-dimethyl-2(3-butynyl)cyclohexanone, 91.8 ml water, 6.7 g sulfuric acid (concentrated), 1.3 g mercuric sulfate and 168 ml of methanol is stirred at room temperature for a period of 1.5 hours. The resulting reaction mass is then extracted with five 100 ml portions of diethyl ether and the ether extracts are combined, dried over anhydrous sodium sulfate and evaporated to yield 28 g of 2,6-dimethyl-2,3(oxobutyl)cyclohexanone having the structure:

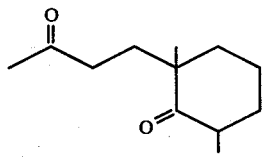

as confirmed by Infrared analysis.

Part D: Production of trans-8,10-dimethyl(9)octal-2-one

Reaction:

 

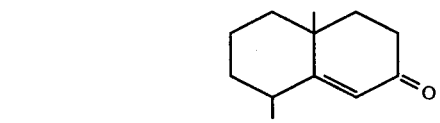

Procedure

A mixture of 27.0 g of 2,6-dimethyl-2,3-oxobutyl cyclohexanone is intimately admixed with 9.37 g of sodium ethoxide and 500 ml food grade ethyl alcohol and the resulting mixture is added under a nitrogen blanket for 1 hour at 45°–50° C. After the 1 hour period, 500 ml water is added and the reaction mass is extracted with five 100 ml portions of diethyl ether. The combined ether extracts are washed with water to a pH of 7 and concentrated to yield 23.0 g of crude product.

This material is distilled to yield 16 g product, b.p. 70°–77° C (0.15 mm Hg) having the structure:

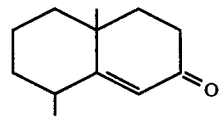

Part E: Production of 2-ethynyl-8,10-dimethyl(α)octal-2-ol

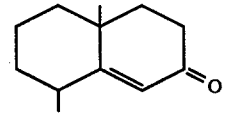

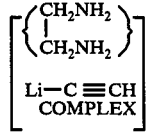

-continued

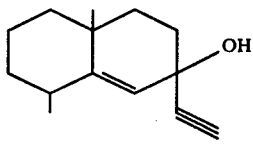

Procedure

Into a 2 liter reaction flask is placed 720 ml dioxane and acetylene is passed into the dioxane for 1 hour. The solution is stirred as 123.28 g (1.34 moles) of lithium acetylide-ethylene diamine complex is added. 12.0 g of the trans-8,10-dimethyl(9)octal-2-one produced according to Part D in 100 ml dioxane is then added to the reaction mass over a period of 30 minutes. Passage of acetylene gas into the reaction mass is continued for one hour after the addition. The reaction mass is then stirred at room temperature, blanketed with nitrogen for a period of 24 hours.

750 ml of saturated aqueous ammonium chloride solution is then added slowly to the reaction mass and the organic layer is separated. The aqueous phase is washed with diethyl ether and the ether extract and organic layer are combined. The resulting solution is washed with water until neutral, dried and concentrated to yield 24.0 g of a compound having the structure:

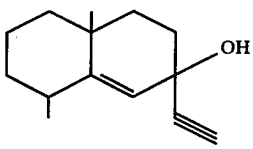

Part F: Production of
2-acetyl-3,4,4a,5,6,7-hexahydro-4a,8-dimethylnaphthalene

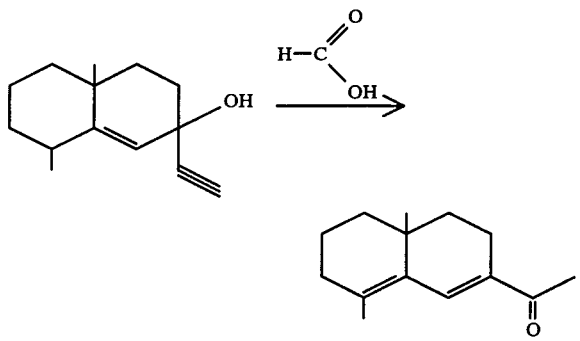

Procedure 24.0 g of the compound having the structure:

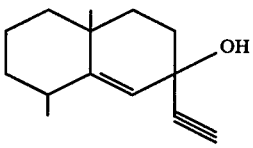

is intimately admixed with 160 ml 98% formic acid. The resulting mixture is refluxed for 2½ hours and then cooled to room temperature and neutralized with saturated aqueous sodium bicarbonate. The resulting mixture is then extracted with five 100 ml portions of diethyl ether. The ether extracts are washed with water until neutral and then concentrated. The resulting crude material, on distillation, gives 1.5 g of material, b.p. 151-155 (0.5 mm Hg); 2-acetyl-3,4,4a,5,6,7-hexahydro-4a,8-dimethylnaphthalene having the structure:

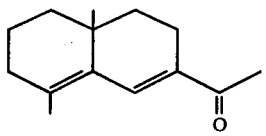

as confirmed by NMR, Infrared and Mass Spectral analyses. The NMR, Infrared and Mass Spectral data are identical to those set forth in Example XII.

What is claimed is:

1. A mixture of compounds defined by the structure:

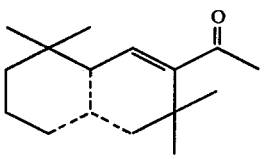

wherein one of the dashed lines is a carbon-carbon double bond, and each of the other of the dashed lines is a carbon-carbon single bond, said mixture consisting essentially of compounds having the structures:

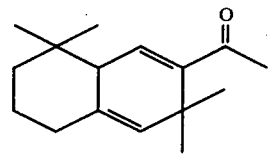

;

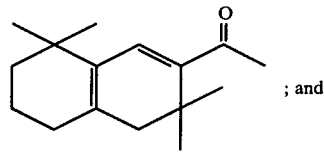

; and

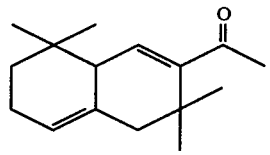

2. A product produced by the process of cyclizing the acetyl conjugated cyclohexadiene having the structure:

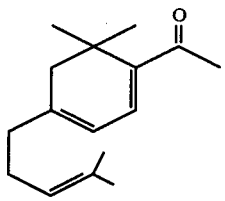

by means of heating said acetyl conjugated cyclohexadiene with a mixture consisting of an acid selected from the group consisting of phosphoric acid, dilute sulfuric acid, borontrifluoride and boron-trifluoride etherate; and a solvent at a temperature in the range of from 70° up to 100° C, the reaction mass containing from 25 up to 50 weight percent of solvent.

* * * * *